(12) United States Patent
Locke et al.

(10) Patent No.: US 11,432,966 B2
(45) Date of Patent: Sep. 6, 2022

(54) COMPOSITE DRESSINGS FOR IMPROVED GRANULATION AND REDUCED MACERATION WITH NEGATIVE-PRESSURE TREATMENT

(71) Applicant: KCI Licensing, Inc., San Antonio, TX (US)

(72) Inventors: Christopher Brian Locke, Bournemouth (GB); Timothy Mark Robinson, Shillingstone (GB); John R. Harper, Boerne, TX (US)

(73) Assignee: KCI Licensing, Inc., San Antonio, TX (US)

( * ) Notice: Subject to any disclaimer, the term of this patent is extended or adjusted under 35 U.S.C. 154(b) by 204 days.

(21) Appl. No.: 15/997,761

(22) Filed: Jun. 5, 2018

(65) Prior Publication Data
US 2018/0353336 A1 Dec. 13, 2018

Related U.S. Application Data

(60) Provisional application No. 62/516,550, filed on Jun. 7, 2017, provisional application No. 62/516,540, filed
(Continued)

(51) Int. Cl.
*A61F 13/00* (2006.01)
*A61F 13/02* (2006.01)
(Continued)

(52) U.S. Cl.
CPC .... *A61F 13/00068* (2013.01); *A61F 13/0216* (2013.01); *A61F 13/0223* (2013.01);
(Continued)

(58) Field of Classification Search
CPC .............. A61F 13/00068; A61F 13/0206
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyethylene-Single-Sided-Medical-Tape-63-Liner/?N=5002385+8729793+3294739632&rt=rud; accessed May 21, 2019>.
(Continued)

*Primary Examiner* — Tatyana Zalukaeva
*Assistant Examiner* — Meagan Ngo

(57) ABSTRACT

Dressings for tissue treatment with negative pressure and methods of using the dressings for tissue treatment with negative pressure, which may comprise a dressing having at least three layers assembled in a stacked relationship. The first layer may comprise or consist essentially of a polymer film having a plurality of fluid restrictions that are normally unstrained or closed. The second layer may comprise a manifold, and the third layer may comprise or consist essentially of a polymer drape. A fourth layer, which may be coupled to the first layer opposite the second layer, may comprise or consist essentially of a silicone gel having a plurality of apertures. In some examples, the plurality of apertures in the fourth layer may be registered with the fluid restrictions of the first layer.

28 Claims, 11 Drawing Sheets

Related U.S. Application Data on Jun. 7, 2017, provisional application No. 62/516,566, filed on Jun. 7, 2017.

(51) Int. Cl.
*A61M 1/00* (2006.01)
*A61F 13/15* (2006.01)
*A61F 13/537* (2006.01)
*A61F 13/534* (2006.01)

(52) U.S. Cl.
CPC ...... *A61F 13/15203* (2013.01); *A61F 13/537* (2013.01); *A61M 1/90* (2021.05); *A61F 13/0206* (2013.01); *A61F 13/0213* (2013.01); *A61F 2013/00217* (2013.01); *A61F 2013/53445* (2013.01); *A61F 2013/53782* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,654,060 A | 4/1972 | Goldman |
| 3,682,180 A | 8/1972 | McFarlane |
| 3,826,254 A | 7/1974 | Mellor |
| 3,930,096 A | 12/1975 | Gilpatrick |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,173,046 A | 11/1979 | Gallagher |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,541,426 A | 9/1985 | Webster |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,983,173 A | 1/1991 | Patience et al. |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,313 A | 5/1994 | Karami et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,352 A | 9/1995 | Nishino et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A | 6/1997 | Fabo |
| 5,636,643 A | 6/1997 | Argenta et al. |
| 5,645,081 A | 7/1997 | Argenta et al. |
| 5,720,714 A | 2/1998 | Penrose |
| 5,842,503 A | 12/1998 | Foley |
| 5,951,505 A | 9/1999 | Gilman et al. |
| 5,981,822 A | 11/1999 | Addison |
| 6,019,511 A | 2/2000 | Thomas et al. |
| 6,071,267 A | 6/2000 | Zamierowski |
| 6,135,116 A | 10/2000 | Vogel et al. |
| 6,241,747 B1 | 6/2001 | Ruff |
| 6,278,036 B1 | 8/2001 | Anhauser et al. |
| 6,287,316 B1 | 9/2001 | Agarwal et al. |
| 6,345,623 B1 | 2/2002 | Heaton et al. |
| 6,468,626 B1 | 10/2002 | Takai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,623,681 B1 | 9/2003 | Taguchi et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 | 12/2010 | Weston |
| 7,867,206 B2 | 1/2011 | Lockwood et al. |
| 7,880,050 B2 | 2/2011 | Robinson et al. |
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |

(56) References Cited

U.S. PATENT DOCUMENTS

| | | |
|---|---|---|
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2001/0043943 A1 | 11/2001 | Coffey |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0203011 A1 | 10/2003 | Abuelyaman et al. |
| 2004/0030304 A1* | 2/2004 | Hunt ............... A61L 15/22 |
| | | 604/317 |
| 2004/0126413 A1 | 7/2004 | Sigurjonsson et al. |
| 2004/0138604 A1 | 7/2004 | Sigurjonsson et al. |
| 2004/0148756 A1 | 8/2004 | Pommer |
| 2004/0261295 A1 | 12/2004 | Meschter |
| 2005/0226917 A1 | 10/2005 | Burton |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2008/0300555 A1 | 12/2008 | Olson et al. |
| 2009/0047495 A1 | 2/2009 | Hubbs |
| 2009/0082746 A1 | 3/2009 | Thomas et al. |
| 2009/0221979 A1 | 9/2009 | Huang et al. |
| 2009/0234307 A1* | 9/2009 | Vitaris ............... A61M 1/0052 |
| | | 604/304 |
| 2009/0293887 A1* | 12/2009 | Wilkes ............... A61F 13/0289 |
| | | 128/888 |
| 2010/0030170 A1 | 2/2010 | Keller et al. |
| 2010/0030178 A1 | 2/2010 | MacMeccan et al. |
| 2010/0036334 A1 | 2/2010 | Heagle et al. |
| 2010/0063484 A1 | 3/2010 | Heagle |
| 2010/0069863 A1* | 3/2010 | Olson ............... A61M 1/0088 |
| | | 604/368 |
| 2010/0069885 A1 | 3/2010 | Stevenson et al. |
| 2010/0106115 A1 | 4/2010 | Hardman et al. |
| 2010/0159192 A1* | 6/2010 | Cotton ............... A61F 13/022 |
| | | 428/137 |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0117178 A1 | 5/2011 | Junginger |
| 2011/0160686 A1 | 6/2011 | Ueda et al. |
| 2011/0178451 A1 | 7/2011 | Robinson et al. |
| 2011/0213287 A1 | 9/2011 | Lattimore et al. |
| 2011/0224631 A1 | 9/2011 | Simmons et al. |
| 2011/0282309 A1 | 11/2011 | Adie et al. |
| 2011/0313374 A1 | 12/2011 | Lockwood et al. |
| 2012/0046603 A1* | 2/2012 | Vinton ............... A61F 13/00051 |
| | | 604/24 |
| 2012/0157945 A1* | 6/2012 | Robinson ............... A61F 13/02 |
| | | 604/319 |
| 2012/0209226 A1 | 8/2012 | Simmons et al. |
| 2012/0238932 A1 | 9/2012 | Atteia et al. |
| 2013/0053748 A1 | 2/2013 | Cotton |
| 2013/0152945 A1 | 6/2013 | Locke et al. |
| 2013/0261534 A1 | 10/2013 | Niezgoda et al. |
| 2014/0031771 A1 | 1/2014 | Locke et al. |
| 2014/0052041 A1 | 2/2014 | Barberio |
| 2014/0058309 A1 | 2/2014 | Addison et al. |
| 2014/0081192 A1 | 3/2014 | Wenske et al. |
| 2014/0094730 A1 | 4/2014 | Greener et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1 | 8/2014 | Von Wolff et al. |
| 2014/0350494 A1 | 11/2014 | Hartwell et al. |
| 2014/0364819 A1 | 12/2014 | VanDelden |
| 2015/0038933 A1 | 2/2015 | Day et al. |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0119833 A1* | 4/2015 | Coulthard ............... A61F 13/00068 |
| | | 604/319 |
| 2015/0141941 A1 | 5/2015 | Allen et al. |
| 2015/0150729 A1 | 6/2015 | Dagger et al. |
| 2015/0174291 A1 | 6/2015 | Zimnitsky et al. |
| 2015/0174304 A1 | 6/2015 | Askem et al. |
| 2015/0290042 A1 | 10/2015 | Freer et al. |
| 2015/0290050 A1 | 10/2015 | Wada |
| 2015/0320434 A1 | 11/2015 | Ingram et al. |
| 2015/0320602 A1 | 11/2015 | Locke et al. |
| 2015/0320603 A1 | 11/2015 | Locke et al. |
| 2016/0000610 A1 | 1/2016 | Riesinger |
| 2016/0015571 A1 | 1/2016 | Robinson et al. |
| 2016/0022885 A1 | 1/2016 | Dunn et al. |
| 2016/0030646 A1 | 2/2016 | Hartwell et al. |
| 2016/0095754 A1 | 4/2016 | Andrews et al. |
| 2016/0144084 A1 | 5/2016 | Collinson et al. |
| 2016/0144085 A1 | 5/2016 | Melin et al. |
| 2016/0166744 A1 | 6/2016 | Hartwell |
| 2016/0175156 A1 | 6/2016 | Locke et al. |
| 2016/0199546 A1 | 7/2016 | Chao |
| 2016/0199550 A1 | 7/2016 | Seddon et al. |
| 2016/0220742 A1 | 8/2016 | Robinson et al. |
| 2016/0262672 A1 | 9/2016 | Hammond et al. |
| 2016/0354253 A1 | 12/2016 | Hunt et al. |
| 2017/0014273 A1 | 1/2017 | Woodroof |
| 2017/0079846 A1 | 3/2017 | Locke et al. |
| 2017/0095374 A1 | 4/2017 | Lauer |
| 2017/0172807 A1 | 6/2017 | Robinson et al. |
| 2017/0174852 A1 | 6/2017 | Hanschen et al. |
| 2017/0209312 A1 | 7/2017 | Kanchagar et al. |
| 2017/0258640 A1 | 9/2017 | Ahsani Ghahreman et al. |
| 2017/0312406 A1 | 11/2017 | Svensby |
| 2017/0348154 A1 | 12/2017 | Robinson et al. |
| 2017/0348158 A1 | 12/2017 | You et al. |
| 2018/0071148 A1 | 3/2018 | Lockwood et al. |
| 2018/0289872 A1 | 10/2018 | Coulthard et al. |
| 2018/0296394 A1 | 10/2018 | Barberio |
| 2019/0184075 A1 | 6/2019 | Roos |

FOREIGN PATENT DOCUMENTS

| | | |
|---|---|---|
| AU | 755496 B2 | 12/2002 |
| CA | 2005436 A1 | 6/1990 |
| CN | 106390213 A | 2/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |

(56) References Cited

FOREIGN PATENT DOCUMENTS

| | | | |
|---|---|---|---|
| EP | 0161865 | A2 | 11/1985 |
| EP | 0174803 | A2 | 3/1986 |
| EP | 0358302 | A2 | 3/1990 |
| EP | 1018967 | A1 | 7/2000 |
| GB | 692578 | A | 6/1953 |
| GB | 2 195 255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| GB | 2468905 | A | 9/2010 |
| JP | 2008073187 | A | 4/2008 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 9319709 | A1 | 10/1993 |
| WO | 94/020041 | A1 | 9/1994 |
| WO | 96/05873 | A1 | 2/1996 |
| WO | 97/18007 | A1 | 5/1997 |
| WO | 99/13793 | A1 | 3/1999 |
| WO | 0185248 | A1 | 11/2001 |
| WO | 2007113597 | A2 | 10/2007 |
| WO | 2009002260 | A1 | 12/2008 |
| WO | 2010061228 | A1 | 6/2010 |
| WO | 2011008497 | A2 | 1/2011 |
| WO | 2011121127 | A1 | 10/2011 |
| WO | 2011127188 | A2 | 10/2011 |
| WO | 2011135286 | A1 | 11/2011 |
| WO | 2014140608 | A1 | 9/2014 |
| WO | 2015098373 | A1 | 7/2015 |
| WO | 2015168681 | A1 | 11/2015 |
| WO | 2015173547 | A1 | 11/2015 |
| WO | 2015193257 | A1 | 12/2015 |
| WO | 2016014645 | A1 | 1/2016 |
| WO | 2016015001 | A2 | 1/2016 |
| WO | 2017040045 | A1 | 3/2017 |
| WO | 2017119996 | A1 | 7/2017 |

OTHER PUBLICATIONS

3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Sided-Thermoplastic-Elastomer-TPE-Medical-Incise-Tape/?N=5002385+4294834151&rt=d; accessed May 21, 2019>.
International Search Report and Written Opinion for related application PCT/US2018/036013, dated Aug. 7, 2018.
International Search Report and Written Opinion for related application PCT/US2018/035945, dated Aug. 24, 2018.
International Search Report and Written Opinion for related application PCT/US2018/036074, dated Aug. 24, 2018.
International Search Report and Written Opinion for related application PCT/US2018/035957, dated Sep. 28, 2018.
International Search Report and Written Opinion for related application PCT/US2018/035995, dated Oct. 1, 2018.
International Search Report and Written Opinion for related application PCT/US2018/036021, dated Aug. 24, 2018.
International Search Report and Written Opinion for related application PCT/US2018/036019, dated Oct. 18, 2018.
International Search Report and Written Opinion for related application PCT/US2018/036054, dated Aug. 24, 2018.
International Search Report and Written Opinion for related application PCT/US2018/036049, dated Aug. 29, 2018.
International Search Report and Written Opinion for related application PCT/US2018/036077, dated Aug. 24, 2018.
International Search Report and Written Opinion for related application PCT/US2018/036129, dated Oct. 8, 2018.

Heit, et al., "Foam Pore Size Is a Critical Interface Parameter of Suction-Based Wound Healing Devices," copyright 2012 by the American Society of Plastic Surgeons (www. PRSJournal.com) (Year: 2011).
Office Action for related U.S. Appl. No. 16/000,284, dated Sep. 23, 2019.
Office Action for related U.S. Appl. No. 16/000,284, dated Jun. 8, 2020.
Office Action for related U.S. Appl. No. 15/997,833, dated Jun. 19, 2020.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. Mar. 2011. pp. 79-93.
Selke et al. Packaging: Polymers for Containers, Encyclopedia of Materials: Science and Technology, Elsevier, 2001, pp. 6646-6652.
Office Action for related U.S. Appl. No. 16/000,368, dated Dec. 14, 2020.
Office Action for related U.S. Appl. No. 15/997,809, dated Aug. 5, 2020.
Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Luis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.

(56) References Cited

OTHER PUBLICATIONS

International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sept. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Office Action for related U.S. Appl. No. 15/997,833, dated Mar. 26, 2021.
Office Action for related U.S. Appl. No. 16/000,215, dated Apr. 12, 2021.
Office Action for related U.S. Appl. No. 15/997,818, dated Jan. 27, 2021.
Office Action for related U.S. Appl. No. 15/997,841, dated Jan. 27, 2021.
Office Action for related U.S. Appl. No. 15/997,809, dated Jan. 28, 2021.
Chinese Office Action for related application 2018800367248, dated Apr. 28, 2021.
Office Action for related U.S. Appl. No. 15/997,833, dated Jun. 7, 2021.
Office Action for related U.S. Appl. No. 15/997,841, dated Jun. 8, 2021.
Chinese Office Action for related application 201880048393X, dated May 26, 2021.
Office Action for related U.S. Appl. No. 15/997,809, dated Jul. 8, 2021.
Chinese Office Action for related application 2018800436430, dated Jun. 8, 2021.
Office Action for related U.S. Appl. No. 15/997,923, dated Jul. 23, 2021.
Office Action for related U.S. Appl. No. 15/997,818, dated Aug. 10, 2021.
Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.
Office action for related U.S. Appl. No. 16/000,002, dated Oct. 4, 2021.
Office Action for related U.S. Appl. No. 15/997,923, dated Nov. 16, 2021.
Office Action for related U.S. Appl. No. 16/000,411, dated Jan. 31, 2022.

(56) References Cited

OTHER PUBLICATIONS

Office Action for related U.S. Appl. No. 16/959,651, dated Feb. 15, 2022.
Japanese Office Action for related application 2019-566886, dated Mar. 29, 2022.
Office Action for related U.S. Appl. No. 16/000,383, dated Mar. 31, 2022.
Pappas et al., "Wettability Tests of Polymer Films and Fabrics and Determination of Their Surface Energy by Contact-Angle Methods," Army Research Laboratory, ARL-TR-4056, Mar. 2007, p. 5.
Baltex, Technical Fabrics & Technical Textile Products, https://www.baltex.co.uk/products/xd-spacer-fabrics/, accessed Apr. 20, 2022.
Yimin Qin, Applications of Advanced Technologies in the Development of Functional Medical Textile Materials, Medical Textile Materials, 2016, pp. 55-70, Woodhead Publishing.
Baltex, Technical Fabrics & Technical Textile Products http://web.archive.org/web/20150118084138/http://www.baltex.co.uk/products/Healthcarefabrics/, 2015.
Office Action for related U.S. Appl. No. 17/204,548, dated Apr. 19, 2022.
Office Action for related application U.S. Appl. No. 15/997,818, dated Jun. 9, 2022.
Japanese Office Action for related application 2019-567267, dated Jun. 7, 2022.
Japanese Office Action for related application 2019-566969, dated Jun. 7, 2020.
Japanese Office Action for related application 2019-567266, dated Jun. 7, 2020.

\* cited by examiner

COMPOSITE DRESSINGS FOR IMPROVED GRANULATION AND REDUCED MACERATION WITH NEGATIVE-PRESSURE TREATMENT

RELATED APPLICATION

This application claims the benefit, under 35 U.S.C. § 119(e), of the filing of U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017 each of which is incorporated herein by reference for all purposes.

TECHNICAL FIELD

The invention set forth in the appended claims relates generally to tissue treatment systems and more particularly, but without limitation, to dressings for tissue treatment with negative pressure and methods of using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating tissue may be a composite of dressing layers, including a polyethylene release film, a perforated silicone gel, a fenestrated polyethylene film, a foam, and an adhesive drape. The fenestration pattern of the polyethylene film can be made in registration with the perforation pattern of at least a central area of the silicone gel. In some embodiments, each of the perforations in the central area may have a width or diameter of about 2 millimeters, and each of the fenestrations in the polyethylene film may be slots having a length of about 3 millimeters and a width of about 0.5 millimeters to about 1 millimeter. The foam may be an open-cell foam, such as a reticulated foam. The foam may also be relatively thin and hydrophobic to reduce the fluid hold capacity of the dressing, which can encourage exudate and other fluid to pass quickly to external storage. The foam layer may also be thin to reduce the dressing profile and increase flexibility, which can enable it to conform to wound beds and other tissue sites under negative pressure. The composite dressing can minimize maceration potential, promote granulation, and provide good manifolding.

More generally, some embodiments may comprise a dressing having at least three layers assembled in a stacked relationship. The first layer may comprise or consist essentially of a polymer film having a plurality of fluid restrictions. The fluid restrictions may be described as imperfect elastomeric valves, which may not completely close and can deform and increase in width if negative pressure is applied, providing less restriction to flow. If negative pressure is stopped or reduced, the fluid restrictions generally return to or approach their original state, providing a higher restriction to fluid flow. The second layer may comprise a manifold, and the third layer may comprise or consist essentially of a polymer drape. A fourth layer, which may be coupled to the first layer opposite the second layer, may comprise or consist essentially of a silicone gel having a plurality of apertures. In some examples, the plurality of apertures in the fourth layer may be aligned with the fluid restrictions of the first layer, and may be aligned one-to-one with the fluid restrictions in some embodiments. At least one of the first and third layers may be configured to be interposed between the first layer and a tissue site.

In some embodiments, the manifold may comprise a foam, and more particularly a reticulated polymer foam. A hydrophobic manifold having a thickness of less than 7 millimeters and a free volume of at least 90% may be suitable for many therapeutic applications.

Polyethylene may be a suitable material for the polymer film of the third layer in some examples. In more specific examples, the polymer film may be a polyethylene having an area density of less than 40 grams per square meter. It may also be advantageous for the polymer film of the third layer to be hydrophobic. In some examples, the polymer film may have a water contact angle of greater than 90 degrees.

The fluid restrictions may comprise a plurality of linear slits or slots in some embodiments. For example, the fluid restrictions may comprise a plurality of linear slots having a length of approximately 4 millimeters or less, and a width of approximately 2 millimeters or less. A length of approximately 3 millimeters and a width of approximately 1 millimeter may be suitable for many therapeutic applications. In some embodiments, the fluid restrictions may be distributed across the polymer film in a uniform pattern, such as a grid of parallel rows and columns. In some embodiments, the fluid restrictions may be distributed across the polymer film in parallel rows and columns, and the rows may be spaced about 3 millimeters apart from each other. The fluid restrictions in each of the rows may also be spaced about 3 millimeters apart from each other in some examples.

Additionally, some embodiments of the third layer may comprise or be coupled to a fluid port, which may be coupled to or configured to be coupled to a fluid conductor. A negative-pressure source may be fluidly coupled to the dressing to provide negative-pressure treatment in some examples.

Some embodiments of a dressing or apparatus may comprise a sealing layer, a fluid control layer adjacent to the sealing layer, a manifold layer adjacent to the fluid control layer, and a cover adjacent to the manifold. The fluid layer may have a plurality of imperfect valves configured to be responsive to a pressure gradient. The sealing layer may have a plurality of apertures positioned to expose the plurality of imperfect valves to a lower surface of the dressing.

Some embodiments may comprise a first layer, a second layer coupled to the first layer, a third layer coupled to the second layer opposite the first layer, and a fourth layer coupled to the first layer opposite the second layer. The first layer may comprise a film formed from a hydrophobic material, and a plurality of fluid passages through the film. The fluid passages may be configured to expand in response to a pressure gradient across the film. The second layer may comprise or consist essentially of a manifold formed from a hydrophobic material. The third layer may comprise a polymer drape, and the fourth layer may be formed from a hydrophobic gel having an area density less than 300 grams per square meter. A plurality of apertures through the fourth layer can be fluidly coupled to at least some of the plurality of fluid passages through the film.

In some embodiments, a dressing for treating a tissue site with negative pressure may include a first layer comprising a film have a flat surface texture, and a plurality of fluid restrictions through the film. The fluid restrictions may be configured to be responsive to a pressure gradient across the film. A second layer may be coupled to the first layer, wherein the second layer may comprise or consist essentially of a manifold. A third layer may be coupled to the second layer opposite the first layer, the third layer comprising a polymer drape. A fourth layer may be coupled to the first layer opposite the second layer, the fourth layer comprising a gel having an area density less than 300 grams per square meter and a hardness between about 5 Shore OO and about 80 Shore OO. A plurality of apertures through the fourth layer may be in registration with the plurality of fluid restrictions through the film.

In some embodiments, an apparatus for treating a tissue site with negative pressure may include a first layer comprising a polythene film having a surface with a height variation of less than 0.2 millimeter over 1 centimeter and a contact angle with water greater than 90 degrees. A plurality of fluid passages through the first layer may be normally restricted and configured to expand in response to a pressure gradient across the first layer. A second layer may be coupled to the first layer, the second layer comprising a reticulated polyurethane ether foam having a free volume of at least 90% and a thickness less than 7 millimeters. A third layer can be coupled to the second layer opposite the first layer, the third layer comprising a polymer drape. A fourth layer can be coupled to the first layer opposite the second layer, the fourth layer comprising a silicone gel having an area density less than 300 grams per square meter and a hardness between about 5 Shore OO and about 80 Shore OO. A plurality of apertures through the fourth layer may be in registration with the plurality of fluid passages in the first layer.

In some embodiments, a dressing for treating a tissue site may comprise a cover, a manifold, a perforated polymer film having a substantially flat surface, and a perforated silicone gel having a substantially flat surface. The cover, the manifold, the perforated polymer film, and the perforated silicone gel may be assembled in a stacked relationship with the cover and the perforated silicone gel enclosing the manifold and the perforated polymer film, and the perforated silicone gel can be configured to contact the tissue site. The substantially flat surface of the perforated polymer film may have height variations not exceeding 0.2 millimeters over 1 centimeter in some embodiments, and the substantially flat surface of the perforated silicone gel may have height variations not exceeding 0.2 millimeters over 1 centimeter in some embodiments. In some embodiments, at least one of the perforated polymer film and the perforated silicone gel may be configured to be interposed between the manifold and a tissue site.

In some embodiments, a dressing may include a first layer comprising a manifold, a second layer comprising a hydrophobic film having a plurality of elastomeric valves that are configured to open in response to a pressure gradient across the hydrophobic film, a third layer coupled to the second layer opposite the first layer, and a cover coupled to the first layer opposite the second layer. The third layer may comprise or consist essentially of a hydrophobic gel having a plurality of apertures.

A method of treating a surface wound with negative pressure may comprise applying a dressing as described to the surface wound, sealing the dressing to epidermis adjacent to the surface wound, fluidly coupling the dressing to a source of negative-pressure, and applying negative-pressure from the negative-pressure source to the dressing. In some examples, the dressing may be applied across an edge of the surface wound, without cutting or trimming the dressing.

A method of promoting granulation in a surface wound may comprise applying a dressing to the surface wound, the dressing comprising a cover, a manifold, a perforated polymer film having a substantially flat surface, and a perforated silicone gel having a substantially flat surface. The perforated silicone gel may be sealed to a periwound adjacent to the surface wound, and the cover may be attached to epidermis around the perforated silicone gel. A negative-pressure source may be fluidly coupled to the dressing, and negative pressure from the negative-pressure source may be applied to the dressing. In some embodiments, the dressing may remain on the surface wound for at least 5 days, and at least 7 days in some embodiments. In some embodiments, a wound filler may be disposed between the perforated silicone gel and the surface wound. For example, a foam wound filler may be applied to the surface wound interior to the periwound.

Advantages of the claimed subject matter over the state of the art include: (1) increased formation of granulation tissue (i.e. faster healing), (2) reduced peal force required to remove the dressing (i.e. ease of use, less pain during dressing changes), (3) reduced time to apply the dressing (i.e. ease of use), and/or (4) reduced risk of maceration of the periwound area during treatment, any or all of which may enable a 7-day dressing (versus 48 hour dressing changes), increase therapy compliance, and decrease costs of care. Other objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, and may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
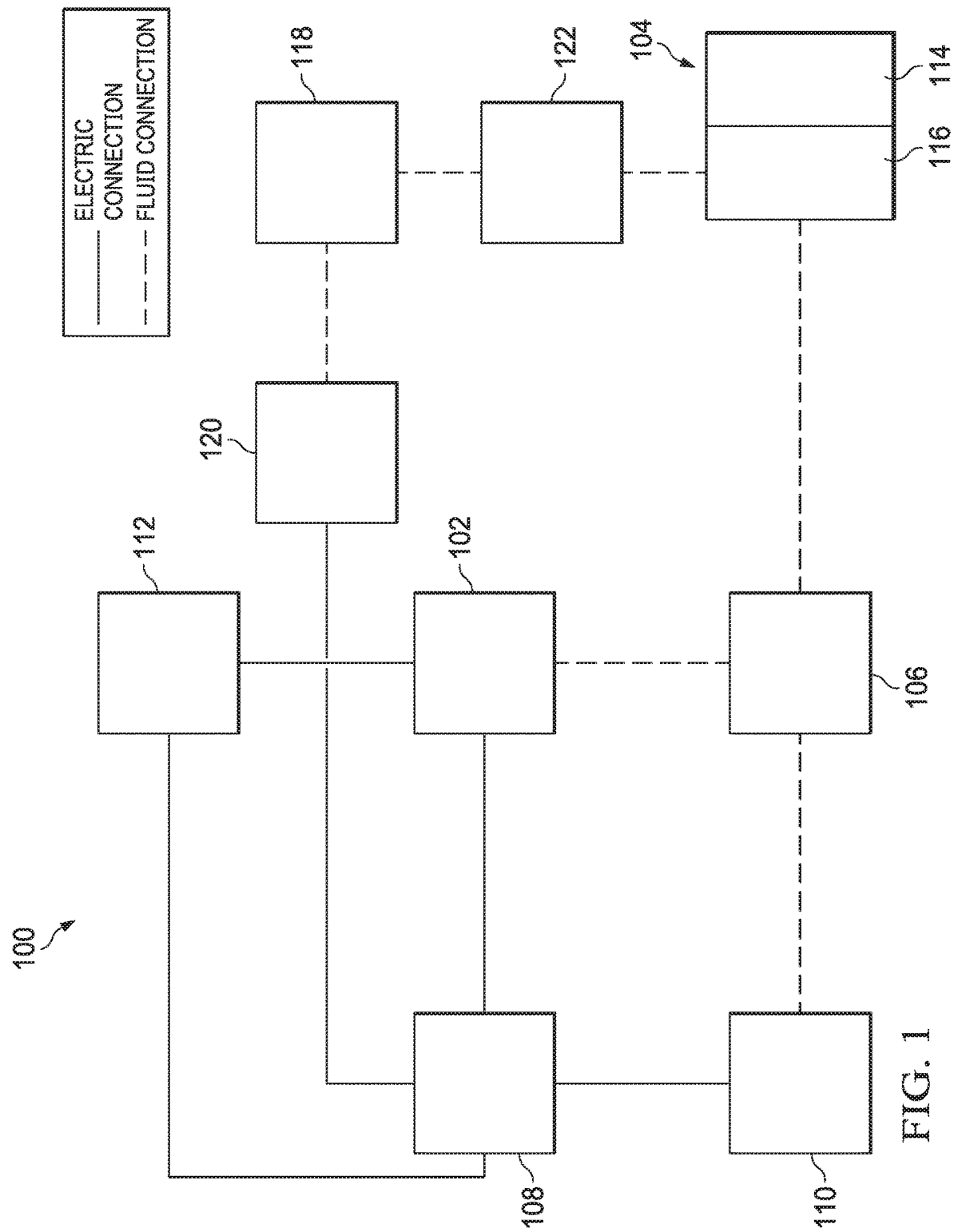
FIG. 1 is a functional block diagram of an example embodiment of a therapy system that can provide tissue treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of one or more dressing layers, such as a tissue interface 114, a cover 116, or both in some embodiments.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108 and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108. The negative-pressure source maybe fluidly coupled to one or more distribution components, which provide a fluid path to a tissue site. In some embodiments, components may also be coupled by virtue of physical proximity, being integral to a single structure, or being formed from the same piece of material.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components, including sensors and data communication devices. In some embodiments, for example, a dressing interface may facilitate coupling a fluid conductor to the dressing 104. For example, such a dressing interface may be a SENSA-T.R.A.C.™ Pad available from KCI of San Antonio, Tex.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−9.9 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezo-resistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms and have more than one layer in some embodiments. The tissue interface 114 may also have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, Calif.; polyether block polyamide copolymer (PEBAX), for example, from Arkema, France; Inspire 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site, such as a surface wound. In some embodiments, for example, some or all of the cover 116 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
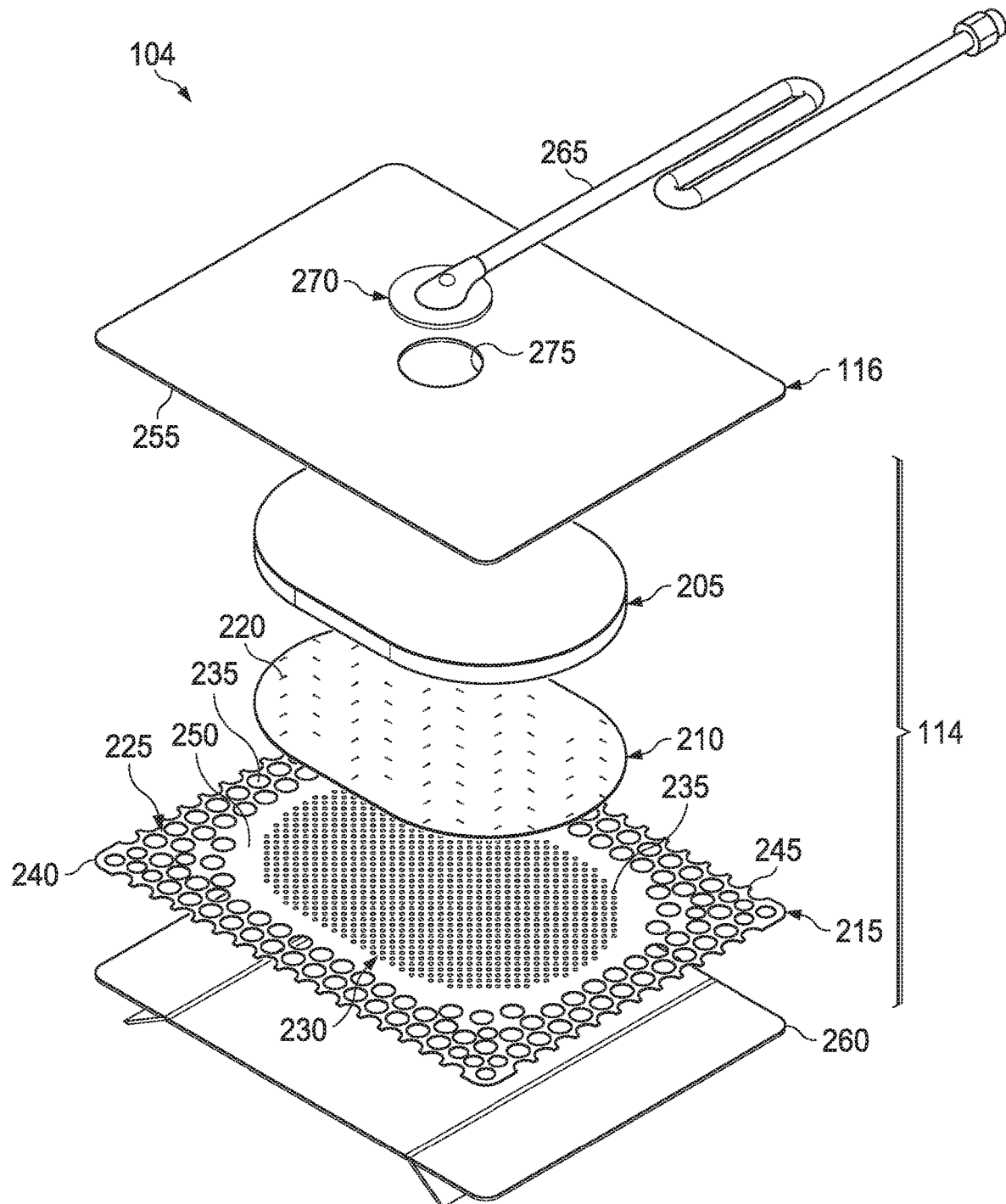
FIG. 2 is an assembly view of an example of a dressing, illustrating additional details that may be associated with some example embodiments of the therapy system of FIG. 1.

FIG. 2 is an assembly view of an example of the dressing 104 of FIG. 1, illustrating additional details that may be associated with some embodiments in which the tissue interface 114 comprises more than one layer. In the example of FIG. 2, the tissue interface 114 comprises a first layer 205, a second layer 210, and a third layer 215. In some embodiments, the first layer 205 may be disposed adjacent to a second layer 210, and the third layer 215 may be disposed adjacent to the second layer 210 opposite the first layer 205. For example, the first layer 205, the second layer 210, and the third layer 215 may be stacked so that the first layer 205 is in contact with the second layer 210, and the second layer 210 is in contact with the first layer 205 and the third layer 215. One or more of the first layer 205, the second layer 210, and the third layer 215 may also be bonded to an adjacent layer in some embodiments.

The first layer 205 may comprise or consist essentially of a manifold or manifold layer, which provides a means for collecting or distributing fluid across the tissue interface 114 under pressure. For example, the first layer 205 may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 114.

In some illustrative embodiments, the first layer 205 may comprise a plurality of pathways, which can be interconnected to improve distribution or collection of fluids. In some embodiments, the first layer 205 may comprise or consist essentially of a porous material having interconnected fluid pathways. For example, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the first layer 205 may additionally or alternatively comprise projections that form interconnected fluid pathways. For example, the first layer 205 may be molded to provide surface projections that define interconnected fluid pathways. Any or all of the surfaces of the first layer 205 may have an uneven, coarse, or jagged profile In some embodiments, the first layer 205 may comprise or consist essentially of a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns (40-50 pores per inch) may be particularly suitable for some types of therapy. The tensile strength of the first layer 205 may also vary according to needs of a prescribed therapy. For example, the tensile strength of a foam may be increased for instillation of topical treatment solutions. The 25% compression load deflection of the first layer 205 may be at least 0.35 pounds per square inch, and the 65% compression load deflection may be at least 0.43 pounds per square inch. In some embodiments, the tensile strength of the first layer 205 may be at least 10 pounds per square inch. The first layer 205 may have a tear strength of at least 2.5 pounds per inch. In some embodiments, the first layer 205 may be a foam comprised of polyols such as polyester or polyether, isocyanate such as toluene diisocyanate, and polymerization modifiers such as amines and tin compounds. In one non-limiting example, the first layer 205 may be a reticulated polyurethane ether foam such as used in GRANUFOAM™ dressing or V.A.C. VERAFLO™ dressing, both available from KCI of San Antonio, Tex.

The thickness of the first layer 205 may also vary according to needs of a prescribed therapy. For example, the thickness of the first layer 205 may be decreased to relieve stress on other layers and to reduce tension on peripheral tissue. The thickness of the first layer 205 can also affect the conformability of the first layer 205. In some embodiments, a thickness in a range of about 5 millimeters to 10 millimeters may be suitable.

The second layer 210 may comprise or consist essentially of a means for controlling or managing fluid flow. In some embodiments, the second layer may comprise or consist essentially of a liquid-impermeable, elastomeric material. For example, the second layer 210 may comprise or consist essentially of a polymer film. The second layer 210 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the second layer may have a substantially flat surface, with height variations limited to 0.2 millimeters over a centimeter.

In some embodiments, the second layer 210 may be hydrophobic. The hydrophobicity of the second layer 210 may vary, but may have a contact angle with water of at least ninety degrees in some embodiments. In some embodiments the second layer 210 may have a contact angle with water of no more than 150 degrees. For example, in some embodiments, the contact angle of the second layer 210 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTA125, FTA200, FTA2000, and FTA4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the second layer 210 may be further enhanced with a hydrophobic coating of other materials, such as silicones and fluorocarbons, either as coated from a liquid, or plasma coated.

The second layer 210 may also be suitable for welding to other layers, including the first layer 205. For example, the second layer 210 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the second layer 210 may vary according to a prescribed therapy or application. In some embodiments, an area density of less than 40 grams per square meter may be suitable, and an area density of about 20-30 grams per square meter may be particularly advantageous for some applications.

In some embodiments, for example, the second layer 210 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the second layer 210 may have one or more fluid restrictions 220, which can be distributed uniformly or randomly across the second layer 210. The fluid restrictions 220 may be bi-directional and pressure-responsive. For example, the fluid restrictions 220 can generally comprise or consist essentially of an elastic passage that is normally unstrained to substantially reduce liquid flow, and can expand in response to a pressure gradient. In some embodiments, the fluid restrictions 220 may comprise or consist essentially of perforations in the second layer 210. Perforations may be formed by removing material from the second layer 210. For example, perforations may be formed by cutting through the second layer 210, which may also deform the edges of the perforations in some embodiments. In the absence of a pressure gradient across the perforations, the passages may be sufficiently small to form a seal or flow restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the second layer 210 may be a suitable valve for some applications. Fenestrations may also be formed by removing material from the second layer 210, but the amount of material removed and the resulting dimensions of the fenestrations may be an order of magnitude less than perforations, and may not deform the edges.

For example, some embodiments of the fluid restrictions 220 may comprise or consist essentially of one or more slots or combinations of slots in the second layer 210. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeter may be particularly suitable for many applications. A tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

The third layer 215 may be a sealing layer comprising or consisting essentially of a soft, pliable material suitable for providing a fluid seal with a tissue site, and may have a substantially flat surface. For example, the third layer 215 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the third layer 215 may have a thickness between about 200 microns (μm) and about 1000 microns (μm). In some embodiments, the third layer 215 may have a hardness between about 5 Shore OO and about 80 Shore OO. Further, the third layer 215 may be comprised of hydrophobic or hydrophilic materials.

In some embodiments, the third layer 215 may be a hydrophobic-coated material. For example, the third layer 215 may be formed by coating a spaced material, such as, for example, woven, nonwoven, molded, or extruded mesh with a hydrophobic material. The hydrophobic material for the coating may be a soft silicone, for example.

The third layer 215 may have a periphery 225 surrounding or around an interior portion 230, and apertures 235 disposed through the periphery 225 and the interior portion 230. The interior portion 230 may correspond to a surface area of the first layer 205 in some examples. The third layer 215 may also have corners 240 and edges 245. The corners 240 and the edges 245 may be part of the periphery 225. The third layer 215 may have an interior border 250 around the interior portion 230, disposed between the interior portion 230 and the periphery 225. The interior border 250 may be substantially free of the apertures 235, as illustrated in the example of FIG. 2. In some examples, as illustrated in FIG. 2, the interior portion 230 may be symmetrical and centrally disposed in the third layer 215.

The apertures 235 may be formed by cutting or by application of local RF or ultrasonic energy, for example, or by other suitable techniques for forming an opening. The apertures 235 may have a uniform distribution pattern, or may be randomly distributed on the third layer 215. The apertures 235 in the third layer 215 may have many shapes, including circles, squares, stars, ovals, polygons, slits, complex curves, rectilinear shapes, triangles, for example, or may have some combination of such shapes.

Each of the apertures 235 may have uniform or similar geometric properties. For example, in some embodiments, each of the apertures 235 may be circular apertures, having substantially the same diameter. In some embodiments, the diameter of each of the apertures 235 may be between about 1 millimeter to about 50 millimeters. In other embodiments, the diameter of each of the apertures 235 may be between about 1 millimeter to about 20 millimeters.

In other embodiments, geometric properties of the apertures 235 may vary. For example, the diameter of the apertures 235 may vary depending on the position of the apertures 235 in the third layer 215, as illustrated in FIG. 2. In some embodiments, the diameter of the apertures 235 in the periphery 225 of the third layer 215 may be larger than the diameter of the apertures 235 in the interior portion 230 of the third layer 215. For example, in some embodiments, the apertures 235 disposed in the periphery 225 may have a diameter between about 9.8 millimeters to about 10.2 millimeters. In some embodiments, the apertures 235 disposed in the corners 240 may have a diameter between about 7.75 millimeters to about 8.75 millimeters. In some embodiments, the apertures 235 disposed in the interior portion 230 may have a diameter between about 1.8 millimeters to about 2.2 millimeters.

At least one of the apertures 235 in the periphery 225 of the third layer 215 may be positioned at the edges 245 of the periphery 225, and may have an interior cut open or exposed at the edges 245 that is in fluid communication in a lateral direction with the edges 245. The lateral direction may refer to a direction toward the edges 245 and in the same plane as the third layer 215. As shown in the example of FIG. 2, the apertures 235 in the periphery 225 may be positioned proximate to or at the edges 245 and in fluid communication in a lateral direction with the edges 245. The apertures 235 positioned proximate to or at the edges 245 may be spaced substantially equidistant around the periphery 225 as shown in the example of FIG. 2. Alternatively, the spacing of the apertures 235 proximate to or at the edges 245 may be irregular.

In the example of FIG. 2, the dressing 104 may further include an attachment device, such as an adhesive 255. The adhesive 255 may be, for example, a medically-acceptable, pressure-sensitive adhesive that extends about a periphery, a portion, or the entire cover 116. In some embodiments, for example, the adhesive 255 may be an acrylic adhesive having a coating weight between 25-65 grams per square meter (g.s.m.). Thicker adhesives, or combinations of adhesives, may be applied in some embodiments to improve the seal and reduce leaks. The adhesive 255 may be a layer having substantially the same shape as the periphery 225. In some embodiments, such a layer of the adhesive 255 may be continuous or discontinuous. Discontinuities in the adhesive 255 may be provided by apertures or holes (not shown) in the adhesive 136. The apertures or holes in the adhesive 255 may be formed after application of the adhesive 255 or by coating the adhesive 255 in patterns on a carrier layer, such as, for example, a side of the cover 116. Apertures or holes in the adhesive 255 may also be sized to enhance the MVTR of the dressing 104 in some example embodiments.

As illustrated in the example of FIG. 2, in some embodiments, a release liner 260 may be attached to or positioned adjacent to the third layer 215 to protect the adhesive 255 prior to use. The release liner 260 may also provide stiffness to assist with, for example, deployment of the dressing 104. The release liner 260 may be, for example, a casting paper, a film, or polyethylene. Further, in some embodiments, the release liner 260 may be a polyester material such as polyethylene terephthalate (PET), or similar polar semi-crystalline polymer. The use of a polar semi-crystalline polymer for the release liner 260 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization. In some embodiments, the release liner 260 may have a surface texture that may be imprinted on an adjacent layer, such as the third layer 215. Further, a release agent may be disposed on a side of the release liner 260 that is configured to contact the third layer 215. For example, the release agent may be a silicone coating and may have a release factor suitable to facilitate removal of the release liner 260 by hand and without damaging or deforming the dressing 104. In some embodiments, the release agent may be a fluorocarbon or a fluorosilicone, for example. In other embodiments, the release liner 260 may be uncoated or otherwise used without a release agent.

FIG. 2 also illustrates one example of a fluid conductor 265 and a dressing interface 270. As shown in the example of FIG. 2, the fluid conductor 265 may be a flexible tube, which can be fluidly coupled on one end to the dressing interface 270. The dressing interface 270 may be an elbow connector, as shown in the example of FIG. 2, which can be placed over an aperture 275 in the cover 116 to provide a fluid path between the fluid conductor 265 and the tissue interface 114.

Figure 3:
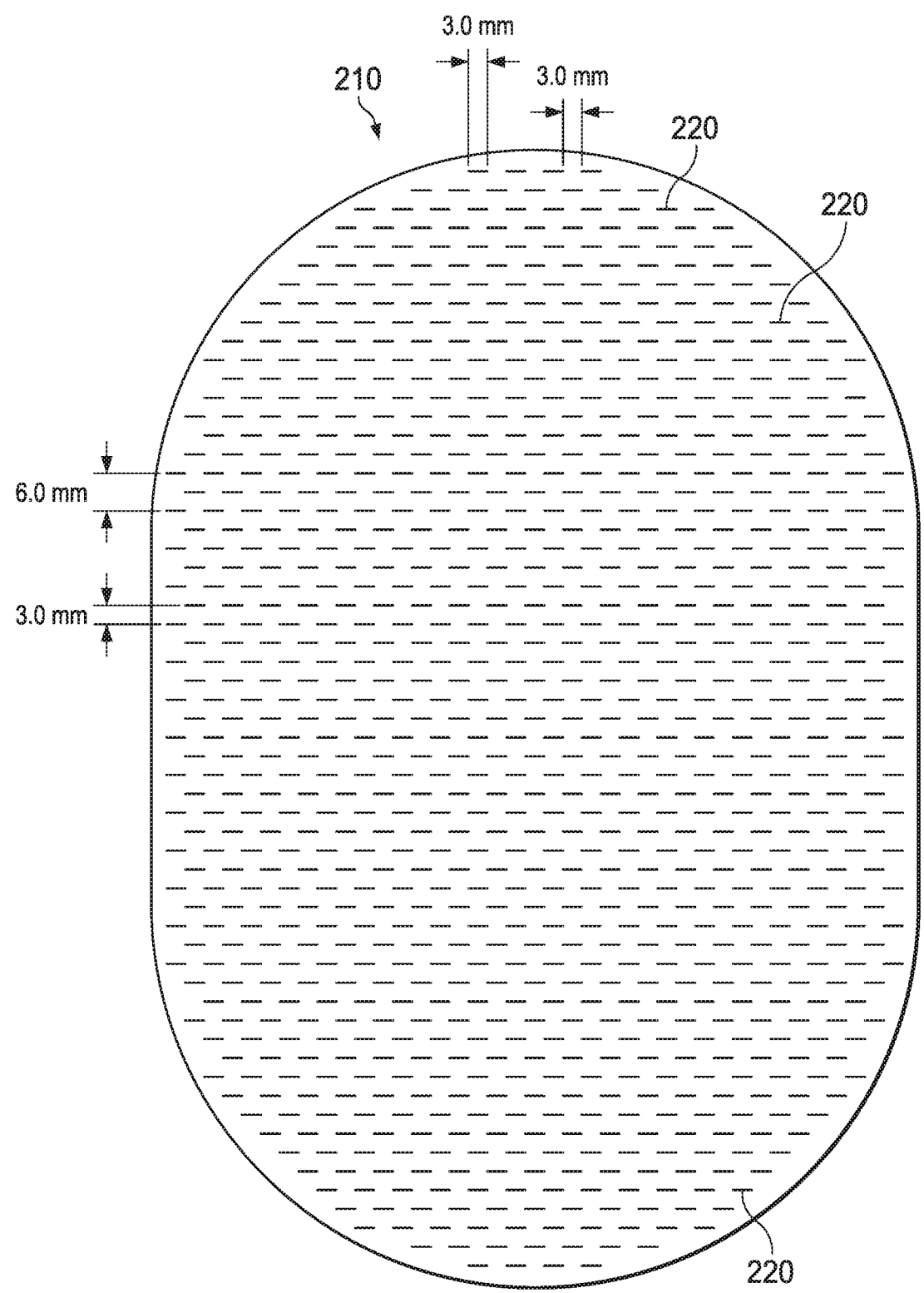
FIG. 3 is a schematic view of an example configuration of fluid restrictions in a layer that may be associated with some embodiments of the dressing of FIG. 2.

FIG. 3 is a schematic view of an example of the second layer 210, illustrating additional details that may be associated with some embodiments. As illustrated in the example of FIG. 3, the fluid restrictions 220 may each consist essentially of one or more linear slots having a length of about 3 millimeters. FIG. 3 additionally illustrates an example of a uniform distribution pattern of the fluid restrictions 220. In FIG. 3, the fluid restrictions 220 are substantially coextensive with the second layer 210, and are distributed across the second layer 210 in a grid of parallel rows and columns, in which the slots are also mutually parallel to each other. In some embodiments, the rows may be spaced about 3 millimeters on center, and the fluid restrictions 220 within each of the rows may be spaced about 3 millimeters on center as illustrated in the example of FIG. 3. The fluid restrictions 220 in adjacent rows may be aligned or offset. For example, adjacent rows may be offset, as illustrated in FIG. 3, so that the fluid restrictions 220 are aligned in alternating rows and separated by about 6 millimeters. The spacing of the fluid restrictions 220 may vary in some embodiments to increase the density of the fluid restrictions 220 according to therapeutic requirements.

Figure 4:
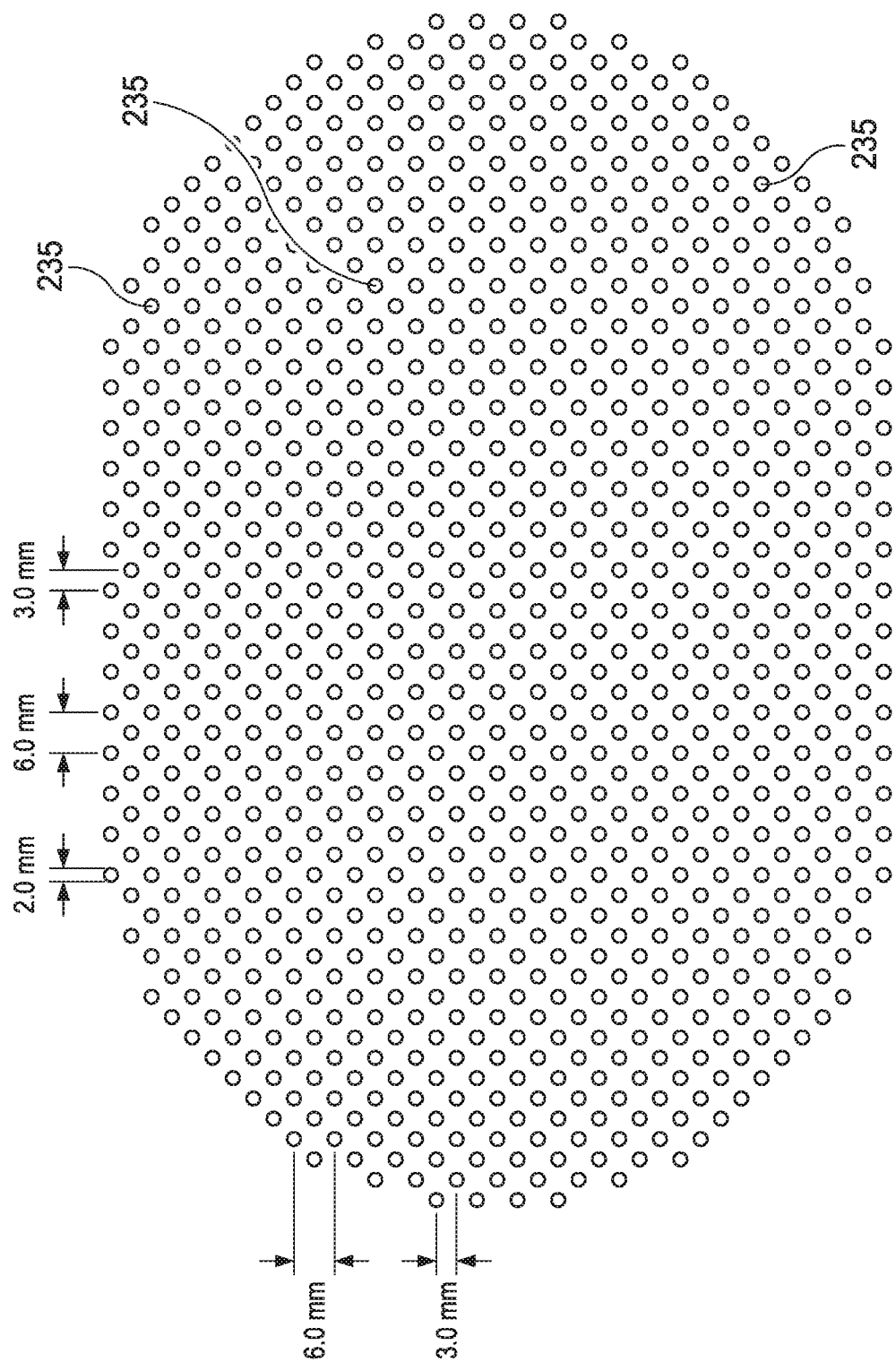
FIG. 4 is a schematic view of an example configuration of apertures in another layer, illustrating additional details that may be associated with some embodiments of the dressing of FIG. 2.

FIG. 4 is a schematic view of an example configuration of the apertures 235, illustrating additional details that may be associated with some embodiments of the third layer 215. In some embodiments, the apertures 235 illustrated in FIG. 4 may be associated only with the interior portion 230. In the example of FIG. 4, the apertures 235 are generally circular and have a diameter of about 2 millimeters. FIG. 4 also illustrates an example of a uniform distribution pattern of the apertures 235 in the interior portion 230. In FIG. 4, the apertures 235 are distributed across the interior portion 230 in a grid of parallel rows and columns. Within each row and column, the apertures 235 may be equidistant from each other, as illustrated in the example of FIG. 4. FIG. 4 illustrates one example configuration that may be particularly suitable for many applications, in which the apertures 235 are spaced about 6 millimeters apart along each row and column, with a 3 millimeter offset.

Figure 5:
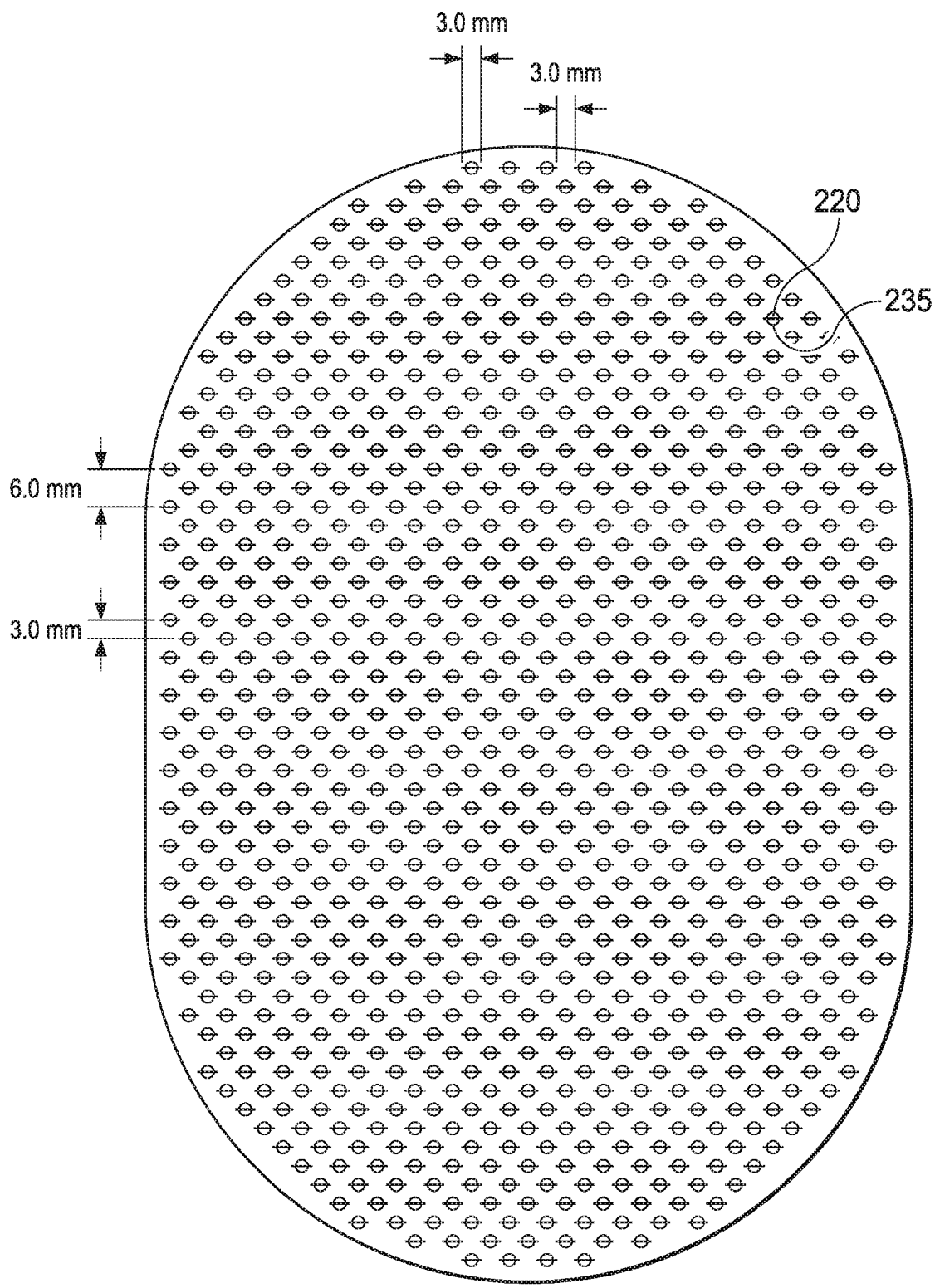
FIG. 5 is a schematic view of the example layer of FIG. 4 overlaid on the example layer of FIG. 3.

FIG. 5 is a schematic view of the example third layer 215 of FIG. 4 overlaid on the second layer 210 of FIG. 3, illustrating additional details that may be associated with some example embodiments of the tissue interface 114. For example, as illustrated in FIG. 5, the fluid restrictions 220 may be aligned, overlapping, in registration with, or otherwise fluidly coupled to the apertures 235 in some embodiments. In some embodiments, one or more of the fluid restrictions 220 may be registered with the apertures 235 only in the interior portion 230, or only partially registered with the apertures 235. The fluid restrictions 220 in the example of FIG. 5 are generally configured so that each of the fluid restrictions 220 is registered with only one of the apertures 235. In other examples, one or more of the fluid restrictions 220 may be registered with more than one of the apertures 235. For example, any one or more of the fluid restrictions 220 may be a perforation or a fenestration that extends across two or more of the apertures 235. Additionally or alternatively, one or more of the fluid restrictions 220 may not be registered with any of the apertures 235.

As illustrated in the example of FIG. 5, the apertures 235 may be sized to expose a portion of the second layer 210, the fluid restrictions 220, or both through the third layer 215. In some embodiments, each of the apertures 235 may be sized to expose no more than two of the fluid restrictions 220. In some examples, the length of each of the fluid restrictions 220 may be substantially equal to or less than the diameter of each of the apertures 235. In some embodiments, the average dimensions of the fluid restrictions 220 are substantially similar to the average dimensions of the apertures 235. For example, the apertures 235 may be elliptical in some embodiments, and the length of each of the fluid restrictions 220 may be substantially equal to the major axis or the minor axis. In some embodiments, though, the dimensions of the fluid restrictions 220 may exceed the dimensions of the apertures 235, and the size of the apertures 235 may limit the effective size of the fluid restrictions 220 exposed to the lower surface of the dressing 104.

One or more of the components of the dressing 104 may additionally be treated with an antimicrobial agent in some embodiments. For example, the first layer 205 may be a foam, mesh, or non-woven coated with an antimicrobial agent. In some embodiments, the first layer may comprise antimicrobial elements, such as fibers coated with an antimicrobial agent. Additionally or alternatively, some embodiments of the second layer 210 may be a polymer coated or mixed with an antimicrobial agent. In other examples, the fluid conductor 265 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Individual components of the dressing 104 may be bonded or otherwise secured to one another with a solvent or non-solvent adhesive, or with thermal welding, for example, without adversely affecting fluid management. Further, the second layer 210 or the first layer 205 may be coupled to the border 250 of the third layer 215 in any suitable manner, such as with a weld or an adhesive, for example.

The cover 116, the first layer 205, the second layer 210, the third layer 215, or various combinations may be assembled before application or in situ. For example, the cover 116 may be laminated to the first layer 205, and the second layer 210 may be laminated to the first layer 205 opposite the cover 116 in some embodiments. The third layer 215 may also be coupled to the second layer 210 opposite the first layer 205 in some embodiments. In some embodiments, one or more layers of the tissue interface 114 may coextensive. For example, the first layer 205 may be coextensive with the second layer 210, as illustrated in the embodiment of FIG. 2. In some embodiments, the dressing 104 may be provided as a single, composite dressing. For example, the third layer 215 may be coupled to the cover 116 to enclose the first layer 205 and the second layer 210, wherein the third layer 215 is configured to face a tissue site.

In use, the release liner 260 (if included) may be removed to expose the third layer 215, which may be placed within, over, on, or otherwise proximate to a tissue site, particularly a surface tissue site and adjacent epidermis. The third layer 215 and the second layer 210 may be interposed between the first layer 205 and the tissue site, which can substantially reduce or eliminate adverse interaction with the first layer 205. For example, the third layer 215 may be placed over a surface wound (including edges of the wound) and undamaged epidermis to prevent direct contact with the first layer 205. Treatment of a surface wound or placement of the dressing 104 on a surface wound includes placing the dressing 104 immediately adjacent to the surface of the body or extending over at least a portion of the surface of the body. Treatment of a surface wound does not include placing the dressing 104 wholly within the body or wholly under the surface of the body, such as placing a dressing within an abdominal cavity. In some applications, the interior portion 230 of the third layer 215 may be positioned adjacent to, proximate to, or covering a tissue site. In some applications, at least some portion of the second layer 210, the fluid restrictions 220, or both may be exposed to a tissue site through the third layer 215. The periphery 225 of the third layer 215 may be positioned adjacent to or proximate to tissue around or surrounding the tissue site. The third layer 215 may be sufficiently tacky to hold the dressing 104 in position, while also allowing the dressing 104 to be removed or re-positioned without trauma to the tissue site.

Removing the release liner 260 can also expose the adhesive 255, and the cover 116 may be attached to an attachment surface. For example, the cover may be attached to epidermis peripheral to a tissue site, around the first layer 205 and the second layer 210. The adhesive 255 may be in fluid communication with an attachment surface through the apertures 235 in at least the periphery 225 of the third layer 215 in some embodiments. The adhesive 255 may also be in fluid communication with the edges 245 through the apertures 235 exposed at the edges 245.

Once the dressing 104 is in the desired position, the adhesive 255 may be pressed through the apertures 235 to bond the dressing 104 to the attachment surface. The apertures 235 at the edges 245 may permit the adhesive 255 to flow around the edges 245 for enhancing the adhesion of the edges 159 to an attachment surface.

In some embodiments, apertures or holes in the third layer 215 may be sized to control the amount of the adhesive 255 in fluid communication with the apertures 235. For a given geometry of the corners 240, the relative sizes of the apertures 235 may be configured to maximize the surface area of the adhesive 255 exposed and in fluid communication through the apertures 235 at the corners 240. For example, as shown in FIG. 2, the edges 245 may intersect at substantially a right angle, or about 90 degrees, to define the corners 240. In some embodiments, the corners 240 may have a radius of about 10 millimeters. Further, in some embodiments, three of the apertures 235 having a diameter between about 7.75 millimeters to about 8.75 millimeters may be positioned in a triangular configuration at the corners 240 to maximize the exposed surface area for the adhesive 255. In other embodiments, the size and number of the apertures 235 in the corners 240 may be adjusted as necessary, depending on the chosen geometry of the corners 240, to maximize the exposed surface area of the adhesive 255. Further, the apertures 235 at the corners 240 may be fully housed within the third layer 215, substantially precluding fluid communication in a lateral direction exterior to the corners 240. The apertures 235 at the corners 240 being fully housed within the third layer 215 may substantially preclude fluid communication of the adhesive 255 exterior to the corners 240, and may provide improved handling of the dressing 104 during deployment at a tissue site. Further, the exterior of the corners 240 being substantially free of the adhesive 136 may increase the flexibility of the corners 240 to enhance comfort.

In some embodiments, the bond strength of the adhesive 255 may vary in different locations of the dressing 104. For example, the adhesive 255 may have a lower bond strength in locations adjacent to the third layer 215 where the apertures 235 are relatively larger, and may have a higher bond strength where the apertures 235 are smaller. Adhesive 255 with lower bond strength in combination with larger apertures 235 may provide a bond comparable to adhesive 255 with higher bond strength in locations having smaller apertures 235.

The geometry and dimensions of the tissue interface 114, the cover 116, or both may vary to suit a particular application or anatomy. For example, the geometry or dimensions of the tissue interface 114 and the cover 116 may be adapted to provide an effective and reliable seal against challenging anatomical surfaces, such as an elbow or heel, at and around a tissue site. Additionally or alternatively, the dimensions may be modified to increase the surface area for the third layer 215 to enhance the movement and proliferation of epithelial cells at a tissue site and reduce the likelihood of granulation tissue in-growth.

Further, the dressing 104 may permit re-application or re-positioning to reduce or eliminate leaks, which can be caused by creases and other discontinuities in the dressing 104 and a tissue site. The ability to rectify leaks may increase the reliability of the therapy and reduce power consumption in some embodiments.

Thus, the dressing 104 in the example of FIG. 2 can provide a sealed therapeutic environment proximate to a tissue site, substantially isolated from the external environment, and the negative-pressure source 102 can reduce the pressure in the sealed therapeutic environment. The third layer 215 may provide an effective and reliable seal against challenging anatomical surfaces, such as an elbow or heel, at and around a tissue site. Further, the dressing 104 may permit re-application or re-positioning, to correct air leaks caused by creases and other discontinuities in the dressing 104, for example. The ability to rectify leaks may increase the efficacy of the therapy and reduce power consumption in some embodiments.

If not already configured, the dressing interface 270 may disposed over the aperture 275 and attached to the cover 116. The fluid conductor 265 may be fluidly coupled to the dressing interface 270 and to the negative-pressure source 102.

Negative pressure applied through the tissue interface 114 can create a negative pressure differential across the fluid restrictions 220 in the second layer 210, which can open or expand the fluid restrictions 220 from their resting state. For example, in some embodiments in which the fluid restrictions 220 may comprise substantially closed fenestrations through the second layer 210, a pressure gradient across the fenestrations can strain the adjacent material of the second layer 210 and increase the dimensions of the fenestrations to allow liquid movement through them, similar to the operation of a duckbill valve. Opening the fluid restrictions 220 can allow exudate and other liquid movement through the fluid restrictions 220 into the first layer 205 and the container 106. Changes in pressure can also cause the first layer 205 to expand and contract, and the interior border 250 may protect the epidermis from irritation. The second layer 210 and the third layer 215 can also substantially reduce or prevent exposure of tissue to the first layer 205, which can inhibit growth of tissue into the first layer 205.

In some embodiments, the first layer 205 may be hydrophobic to minimize retention or storage of liquid in the dressing 104. In other embodiments, the first layer 205 may be hydrophilic. In an example in which the first layer 205 may be hydrophilic, the first layer 205 may also wick fluid away from a tissue site, while continuing to distribute negative pressure to the tissue site. The wicking properties of the first layer 205 may draw fluid away from a tissue site by capillary flow or other wicking mechanisms, for example. An example of a hydrophilic first layer 205 is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

If the negative-pressure source 102 is removed or turned-off, the pressure differential across the fluid restrictions 220 can dissipate, allowing the fluid restrictions 220 to move to their resting state and prevent or reduce the rate at which exudate or other liquid from returning to the tissue site through the second layer 210.

In some applications, a filler may also be disposed between a tissue site and the third layer 215. For example, if the tissue site is a surface wound, a wound filler may be applied interior to the periwound, and the third layer 215 may be disposed over the periwound and the wound filler. In some embodiments, the filler may be a manifold, such as an open-cell foam. The filler may comprise or consist essentially of the same material as the first layer 205 in some embodiments.

Additionally or alternatively, instillation solution or other fluid may be distributed to the dressing 104, which can increase the pressure in the tissue interface 114. The increased pressure in the tissue interface 114 can create a positive pressure differential across the fluid restrictions 220 in the second layer 210, which can open or expand the fluid restrictions 220 from their resting state to allow the instillation solution or other fluid to be distributed to the tissue site.

Figure 6:
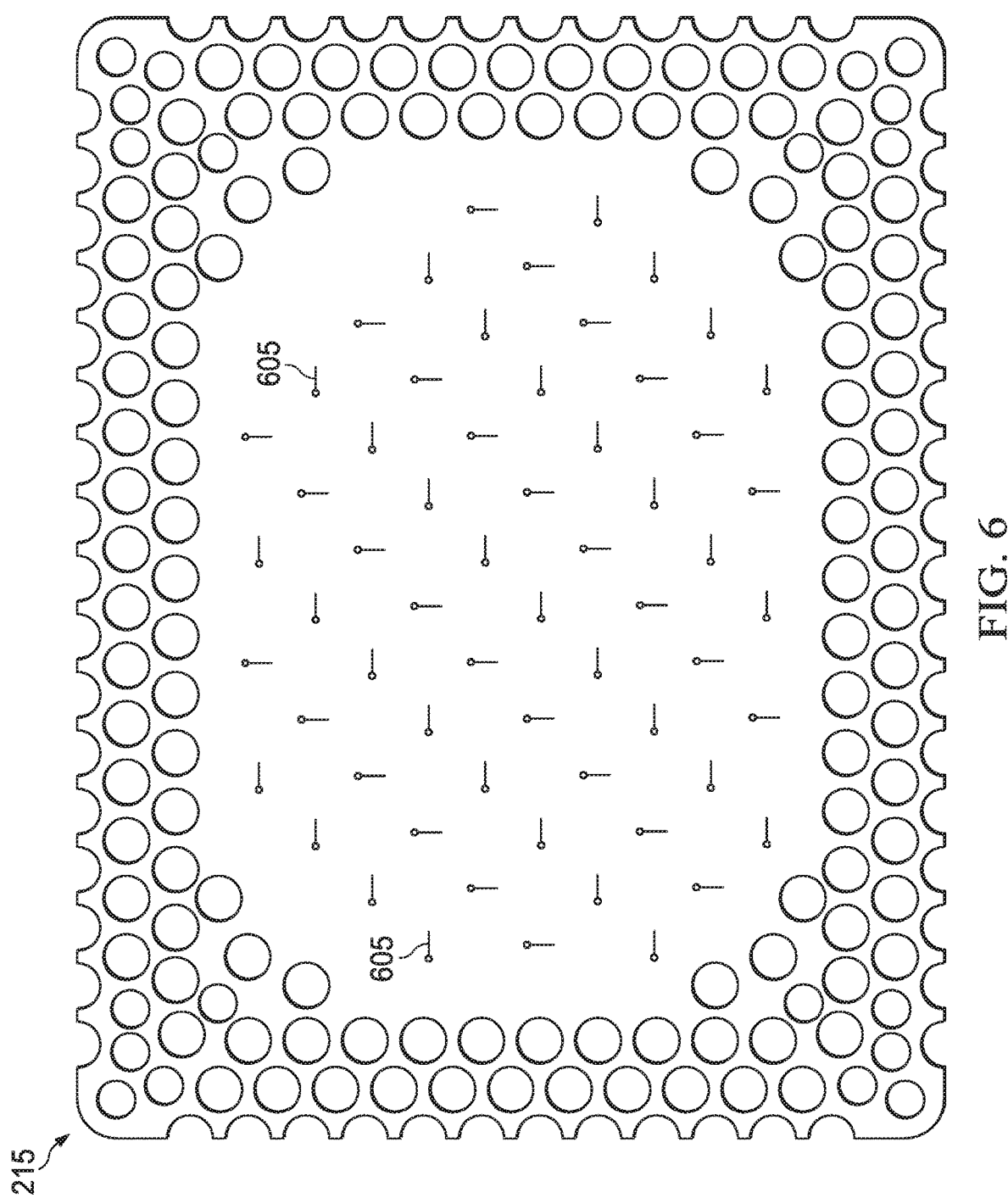
FIG. 6 is a schematic view of another example of another dressing layer, illustrating additional details that may be associated with some embodiments.

FIG. 6 is a schematic view of another example of the third layer 215, illustrating additional details that may be associated with some embodiments. As shown in the example of FIG. 6, the third layer 215 may have one or more fluid restrictions, such as valves 605, instead of or in addition to the apertures 235 in the interior portion 230. Moreover, the valves 605 may be included in the third layer 215 in addition to or instead of the fluid restrictions 220 in the second layer 210. In some embodiments in which the third layer 215 includes one or more of the valves 605, the second layer 210 may be omitted. For example, in some embodiments, the tissue interface 114 may consist essentially of the first layer 205 and the third layer 215 of FIG. 6 with the valves 605 disposed in the interior portion 230.

Figure 7:
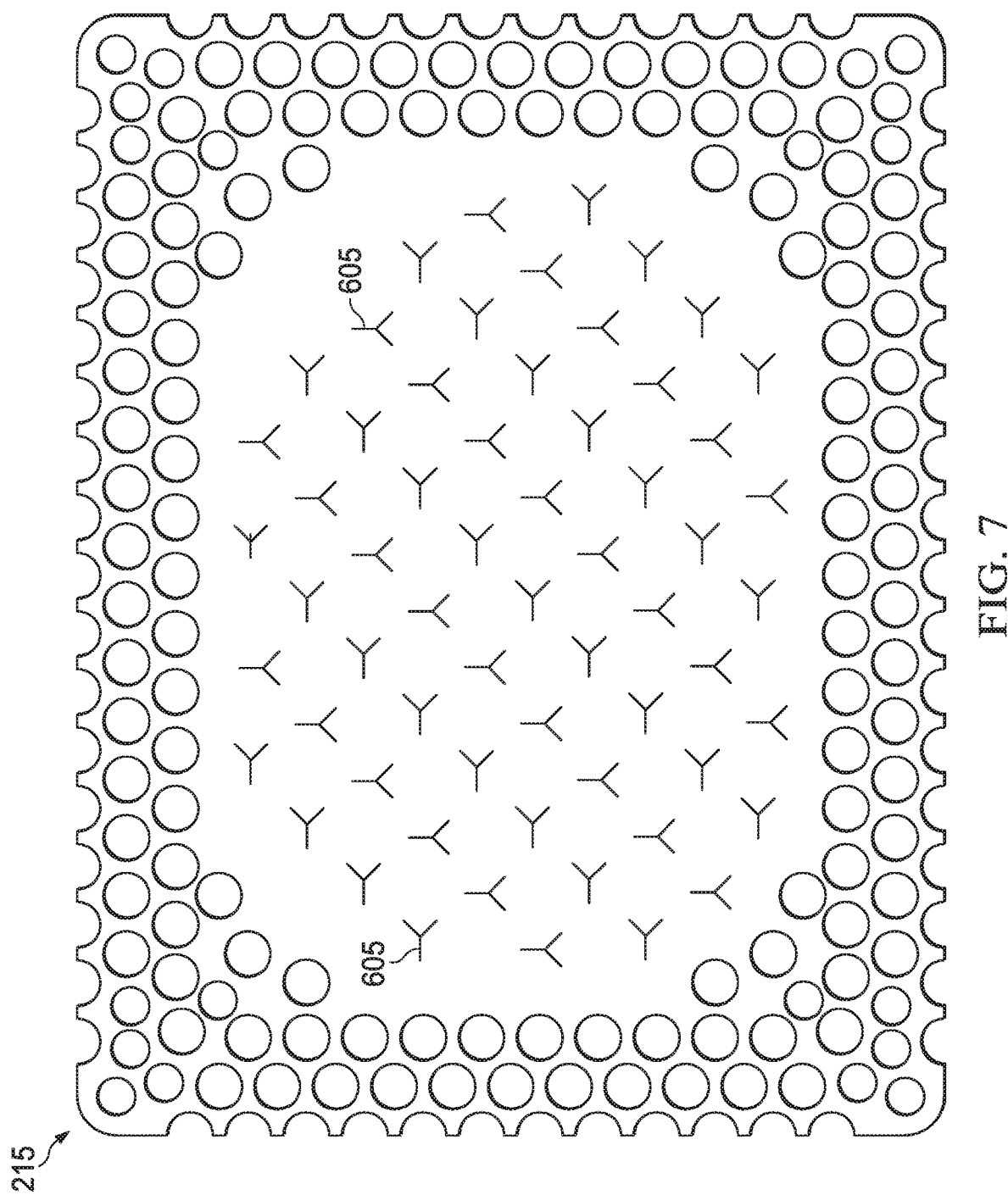
FIG. 7 and FIG. 8 illustrate other example configurations of fluid restrictions that may be associated with some embodiments of layers of the dressing of FIG. 2.
Figure 8:
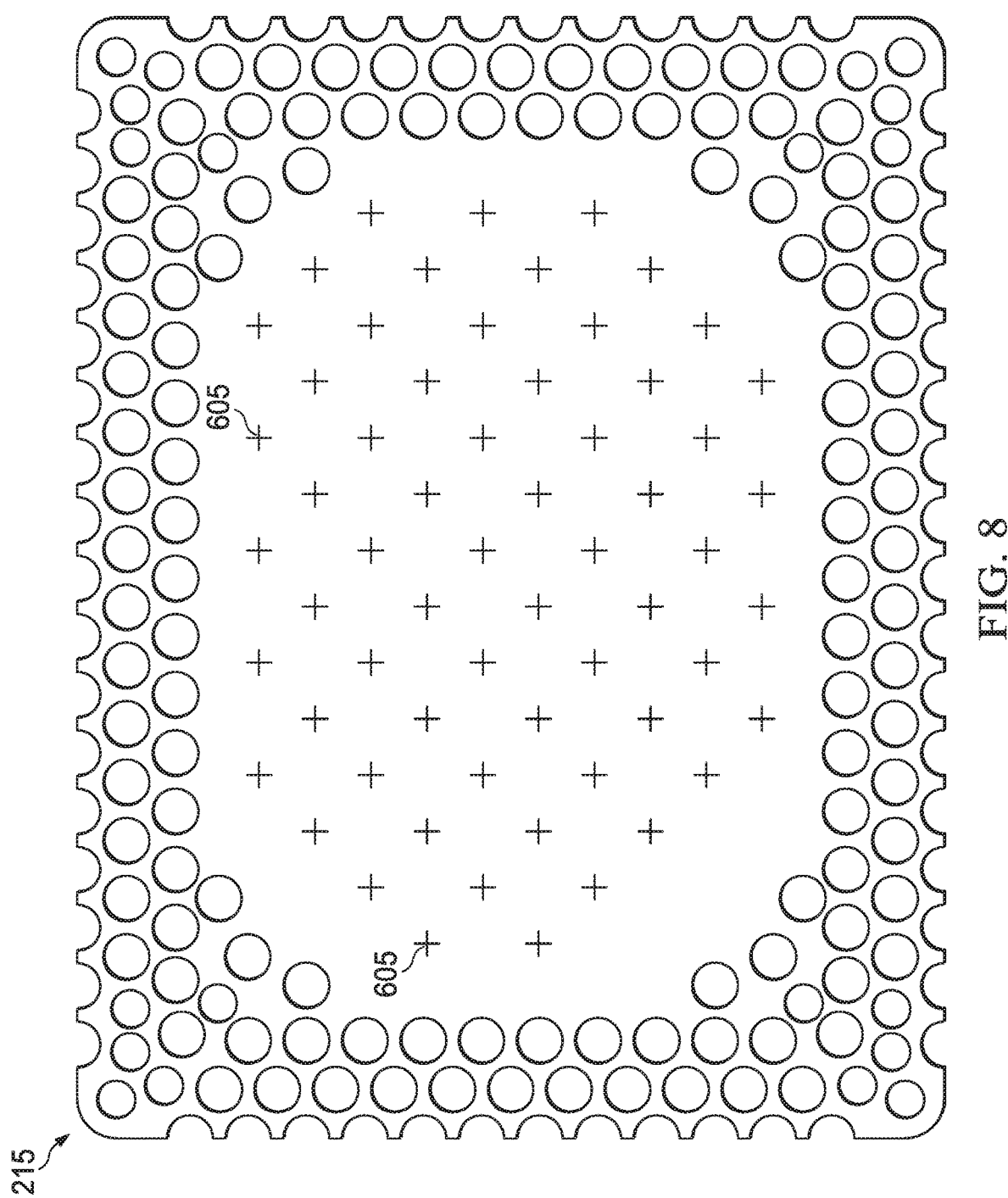

FIG. 7 and FIG. 8 illustrate other example configurations of the valves 605, in which the valves 605 each generally comprise a combination of intersecting slits or cross-slits.

Methods of treating a surface wound to promote healing and tissue granulation may include applying the dressing 104 to a surface wound and sealing the dressing 104 to epidermis adjacent to the surface wound. For example, the third layer 215 may be placed over the surface wound, covering at least a portion of the edge of the surface wound and a periwound adjacent to the surface wound. The cover may also be attached to epidermis around the third layer 215. The dressing 104 may be fluidly coupled to a negative-pressure source, such as the negative-pressure source 102. Negative pressure from the negative-pressure source may be applied to the dressing 104, opening the fluid restrictions 220. The fluid restrictions 220 can be closed by blocking, stopping, or reducing the negative pressure. The second layer 210 and the third layer 215 can substantially prevent exposure of tissue in the surface wound to the first layer 205, inhibiting growth of tissue into the first layer 205. The dressing 104 can also substantially prevent maceration of the periwound.

The systems, apparatuses, and methods described herein may provide significant advantages over prior dressings. For example, some dressings for negative-pressure therapy can require time and skill to be properly sized and applied to achieve a good fit and seal. In contrast, some embodiments of the dressing 104 provide a negative-pressure dressing that is simple to apply, reducing the time to apply and remove. In some embodiments, for example, the dressing 104 may be a fully-integrated negative-pressure therapy dressing that can be applied to a tissue site (including on the periwound) in one step, without being cut to size, while still providing or improving many benefits of other negative-pressure therapy dressings that require sizing. Such benefits may include good manifolding, beneficial granulation, protection of the peripheral tissue from maceration, and a low-trauma and high-seal bond. These characteristics may be particularly advantageous for surface wounds having moderate depth and medium-to-high levels of exudate. Some embodiments of the dressing 104 may remain on the tissue site for at least 5 days, and some embodiments may remain for at least 7 days. Antimicrobial agents in the dressing 104 may extend the usable life of the dressing 104 by reducing or eliminating infection risks that may be associated with extended use, particularly use with infected or highly exuding wounds.

EXAMPLES

Some of the advantages associated with the systems, apparatuses, and methods described herein may be further demonstrated by the following non-limiting example.

Example 1—Evaluation of Dressing in a Swine Model of Full Thickness Excisional Wounds Objective The primary objective of this study was to evaluate an embodiment of a dressing having features described above (designated as "GM" for purposes of the study), in conjunction with V.A.C.® Therapy and V.A.C. VERAFLO™ Therapy as compared to traditional V.A.C.® Therapy with GRANUFOAM™ dressing and to other Advanced Wound Care dressings without V.A.C.® Therapy. Wounds were assessed for granulation tissue formation, presence of maceration in periwound skin and ease of dressing removal as determined by:
  i. Histological assessment for granulation tissue thickness
  ii. Peel strength testing
  iii. Visual assessment of bleeding
  iv. Visual assessment of dressing particles left in wound bed after removal of dressing
  v. Histological assessment for dressing particles, necrosis, bleeding, edema and inflammation
  vi. Maceration (tissue water content) of intact skin
  vii. Histological assessment of intact skin for bacteria, edema and inflammation Test and Control Articles Test Article 1 (TA)

| Description | GM dressing |
|---|---|
| Size | 10 cm × 8 cm foam with 12.5 cm × 11 cm border |
| Storage | Test article stored between 15° C. and 30° C. (59° F. and 86° F.). |

Control Article 1 (CA1)

| | |
|---|---|
| Description | V.A.C. ® GRANUFOAM ™ Dressing |
| Size | ~7.5 cm × 3 cm (cut to fit from larger piece) |
| Storage | Control article stored between 15° C. and 30° C. (59° F. and 86° F.). |

Control Article 2 (CA2)

| | |
|---|---|
| Description | TIELLE ™ non-adhesive advanced wound dressing (AWD) |
| Size | 10 cm × 10 cm |
| Storage | Control article stored between 15° C. and 30° C. (59° F. and 86° F.). |

Control Article 3 (CA3)

| | |
|---|---|
| Description | V.A.C. VERAFLO ™ Dressing |
| Size | ~7.5 cm × 3 cm (cut to fit from larger piece) |
| Storage | Control article stored between 15° C. and 30° C. (59° F. and 86° F.). |

Animal Model

This study was conducted using the animal model outlined below:

| | |
|---|---|
| Species | Sus scrofa scrofa (Porcine) |
| Breed | ½ Duroc, ¼ Landrace cross, ¼ Yorkshire |
| Source | Oak Hill Genetics, Ewing, IL |
| Age at Procedure | Appropriate to weight |
| Weight at Procedure | 50-70 kg or alternate weight as approved by the Study Director |
| Gender | Female (nulliparous and non-pregnant) |
| Number of Animals | 8 + 0 spare |

Study Design

TABLE 1

Study Design

| Group | Number of Animals | Maximum Number of Excisional Wounds Created on Day 0 | Maximum NPWT Sites per Animal | Maximum AWD (Sites per Animal) | Dressing Changes | Peel Testing, Visual Assessment, TEWL | Scheduled Time of Euthanasia |
|---|---|---|---|---|---|---|---|
| 1 | 1 | n = 10/animal | n = 8 | n = 2 | None | Day 4 | Day 4 |
| 2 | 3 | n = 10/animal | n = 8 | n = 2 | None | Day 4 | Day 4 |
| 3 | 4 | n = 10/animal | n = 10 | n = 0$^2$ | Day 4 | Day 4 and Day 7 | Day 7 |

TEWL=transepidermal water loss analysis using Delfin moisture meter; AWD=Advanced Wound Dressing

TABLE 2

Description of Treatment Regimens and Dressings

| Therapy/ Treatment Number | Treatment Abbreviation | Test Material | Therapy |
|---|---|---|---|
| 1 | TANPT$^a$ | TA | Continuous V.A.C. ® Therapy |
| 2 | TANPTI$^a$ | TA | V.A.C. VERAFLO ™ with saline |
| 3 | NPT | CA1 | Continuous V.A.C. ® Therapy |
| 4 | AWD | CA2 | None |
| 5 | NPTI | CA3 | V.A.C. VERAFLO ™ with saline |

$^a$With conductive wires placed on top on intact skin under dressing as appropriate Surgical Procedures Excisional Wound Creation—Day 0

The initial pilot animal (Group 1) underwent all wound creation and therapy prior to scheduling procedures on the additional Group 2 and 3 animals. Up to Ten (10) full thickness skin excisional wounds (~3×7.5 cm) were created on each animal (up to 5 wounds on each side of the spine) with the aid of a sterile template. There was spacing between each of the wounds (approximately 6 cm or more from wound edge to wound edge between adjacent wounds, and sufficient spacing between all wounds to provide enough space to properly place the dressings and the drape. If the length of the back of the animal did not provide enough space for 10 wounds and dressings (determined on Day 0) then 8 wounds (4 on each side of spine) was created. A scalpel blade was used to surgically create the wound down to the subcutaneous fascial layer (just over the muscle) but without disrupting it. If disruption of the subcutaneous fascial layer occurred, it was documented in the study records. Care was taken during wound creation so as not to undermine the perimeter of the wound. The wounds were prepared in two paraspinal columns with efforts made to keep the columns between the crest of the shoulders and the coccygeal tuberosity. Direct pressure with sterile gauze was utilized to obtain hemostasis. In the event of excessive bleeding that did not subside with direct pressure, a hemostat was used to clamp the source of bleeding. Wound sites were kept moist with sterile 0.9% saline-soaked gauze during the creation of other wounds. Wounds were photographed.

Application of Dressings and Negative Pressure Therapy

Following the creation of wounds (Day 0) all wounds received Test or Control Article. On Day 4 (Group 3 only), those wounds undergoing dressing removal received Test or Control Article.

On the designated dressing change day (after peel testing, TEWL, visual observations and photographs), the periwound area was wiped clean with sterile 0.9% saline-soaked gauze and allowed to dry. Dressings were applied to the individual wound sites per a randomization scheme.

An adhesive such as benzoin was placed on the skin surrounding the very perimeter of the test article edges, regardless of the type of dressing for a particular wound, so that the periwound area was framed with adhesive leaving a ~1 cm perimeter of periwound free of benzoin. This means that the immediate periwound skin cannot have benzoin adhesive applied as this may affect the EpiD readings. The adhesive was placed on the skin in any area that V.A.C.® Drape was applied. Alternatively (or in addition to), Hollister (a medical grade silicone adhesive) was applied as an extra adhesive to help maintain a seal.

For the test article wound pair (test article with V.A.C.® Therapy), and/or the test article with V.A.C. VERAFLO™ Therapy (test article using V.A.C. VERAFLO™ Therapy with saline) wounds, a pair of electrodes (e.g. aluminum sheet or wire) was applied so it rested in the peri-wound area (under test article but on top of periwound skin).

As applicable, the skin underneath the strips of the foam bridge were covered with V.A.C.® Drape to protect it. Each bridged wound group was covered with the V.A.C.® Drape included in the dressing kit, one hole will be made in the drape, and a SENSAT.R.A.C.™ Pad or a V.A.C. VERA-T.R.A.C.™ Pad (as applicable) was attached directly above the hole as per instructions for use (IFU). Each of the pads was framed with V.A.C.® Drape along each side to keep it in place and to make sure there was a seal.

A V.A.C.ULTA™ unit was present in the surgical suite on the day of wound creation and was appropriately connected to each pad to verify that each wound group had been sealed properly following the application.

To check the seal around the wounds, negative-pressure wound therapy (NPWT) began at a continuous vacuum pressure of −125 mmHg using the SEAL CHECK™ function on the V.A.C.ULTA™ Unit. Upon verification of a proper seal, the V.A.C.ULTA™ unit was turned off and this procedure was repeated as applicable. Following verification of all seals, additional layers of V.A.C.® Drape was placed around the edges to reinforce the seals and prevent leaks.

For wounds receiving V.A.C. VERAFLO™ Therapy the Fill Assist feature was used to determine the volume of fluid (i.e. saline) required to saturate the dressings in the paired wounds. These determinations were made for wound pairs at each dressing change, as appropriate. V.A.C. VERAFLO™ Therapy NPWT was begun at a continuous vacuum pressure of −125 mmHg using the SEAL CHECK™ function on the V.A.C.ULTA™ Unit. Upon verification of a proper seal, the V.A.C.ULTA™ unit was turned off and this procedure was repeated as applicable. Following verification of all seals, additional layers of V.A.C.® Drape were placed around the edges to reinforce the seals and prevent leaks. The soak/dwell time per cycle was 10 minutes, NPWT time per cycle was 3.5 hours with a target pressure of −125 mmHg.

The entire V.A.C.® Drape-covered area was draped with a tear-resistant mesh (e.g. organza material) secured with V.A.C.® Drape, Elastikon® or equivalent to prevent dislodgement of the dressings.

Interim Dressing Change—Day 4 Group 3 Only

Resistance readings from under the dressings were performed. Peel force testing for wounds were performed on one wound from each treatment pair. The dressings were removed by hand for the other half of each wound pair, unless dressings were intended to stay in place (i.e. TANPT and TANPTI (n=2 animals)). Wound assessments were performed (as applicable) and photographs taken.

Peel Testing and Observations

Peel force testing was performed on one wound from each treatment pair (same wounds as dressing change, if applicable). For wounds where the dressing had been removed, TEWL was performed, wound assessments were performed and photographs taken.

For Groups 1 & 2, (Day 4), peel force testing, TEWL and assessments were performed on 5 wounds. The remaining 5 wounds were collected with dressings in situ for histopathology processing and evaluation.

For Group 3 (Day 7), peel force testing, TEWL and assessments were performed on 5 wounds. The remaining 5 wounds were collected with dressings in situ for histopathology processing and evaluation.

Peel force testing was performed on a tilting operating table. The peel force test was performed using a device that peels back the test material edge while measuring the force that is required to peel the dressing from the wound at an angle of ~180° relative to the peel tester. A digital protractor was used to confirm the angle. The peel strength values indicate the ease with which the test materials can be removed from the wound bed. Removal of the test materials was performed using a 20N Shimpo Digital Force Gauge that was mounted onto a Shimpo Motorized Test Stand and controlled via a computer equipped with LabView.

The drape over the control articles for peel testing was gently circumscribed with a scalpel, taking care to not disrupt the tissue ingrowth into the sides of the dressing. On treatments with the test article for peel testing, a scalpel was used to remove the excess dressing that was not in contact with the wound. This was done by cutting the dressing along the sides, bottom and top where the margins of the wound are visible after negative pressure therapy. The medial end of the dressing or dressing tab was attached to the force gauge with the clip (no circumscribing of the dressing will be performed). The dressing was then pulled from the wound (medial to lateral) at a constant rate from a medial to lateral direction. After the peel force measurements were taken, assessments were performed. Continuous peel force readings were recorded through LabView via the Force Gauge and saved for each wound. Following peel testing, the dressings were saved for analysis of the tissue that remains within the dressing.

Figure 9:
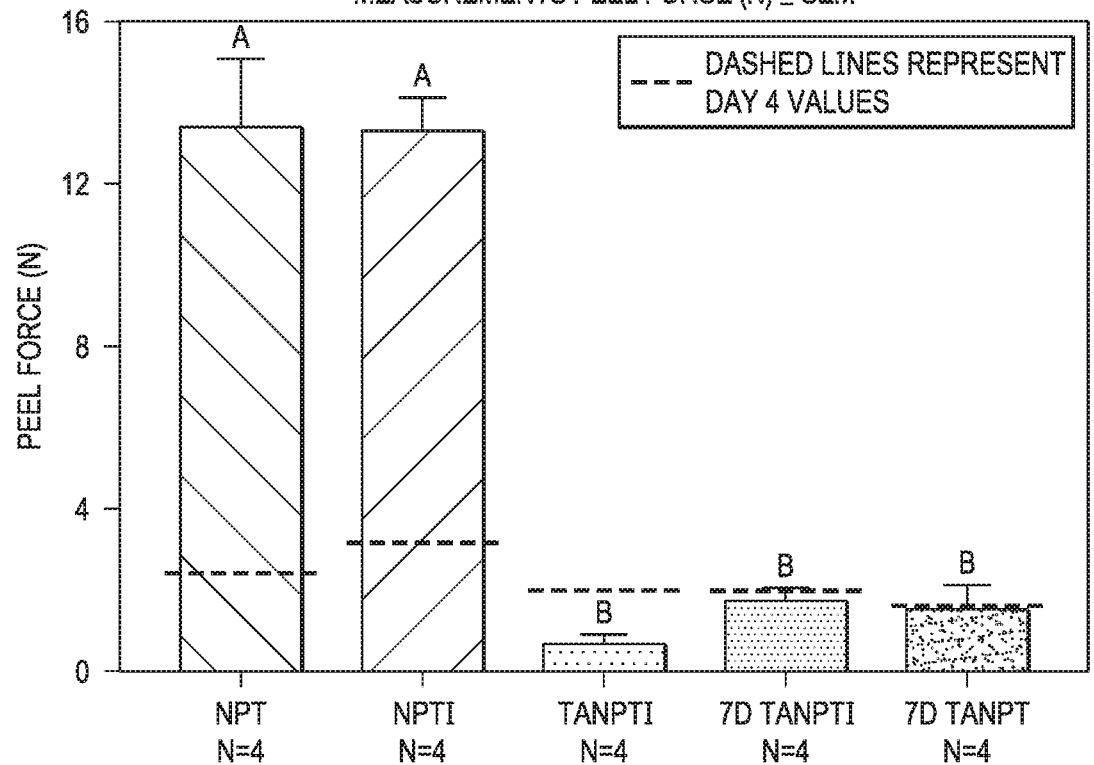
FIG. 9 is a graphical representation of maximum peel force measurements (N) on day 7 following dressing application and removal of each test and control dressing.

FIG. 9 demonstrates the results of maximum peel force measurements (N) on day 7 following dressing application and removal of test articles (designated as "TANPT" and TANPTI) and control dressings. As can be seen, the test article with and without V.A.C. VERAFLO™ Therapy required significantly less peel force.

After peel force testing and TEWL measurements, two biopsy punches (5 mm, or not to exceed 8 mm each) were collected from the center of each wound as applicable.

Transepidermal Water Loss

Determination of the level of moisture at the dressing-skin (intact) interface was performed using a Moisture Meter the EpiD Compact from Delfin Technologies (Kuopio, Finland). This measurement was done immediately after wound creation on Day 0, at the dressing change day (as applicable), and at termination prior to euthanasia. To measure the dielectric constant of the skin, the EpiD Compact instrument was turned used. On the day of wound creation (Day 0), four consecutive measurements of moisture was collected from intact skin on each animal approximating midway between the wound and edge of the wound pad of where the test article and the advanced wound dressings were. On dressing change day and at termination (as applicable), four consecutive measurements of moisture were collected. These measurements were repeated on each of the available wound sites for each animal. All of the measurements/data was recorded.

Wound Assessments

Gross Observations

Wound observations were performed and documented at the dressing change and/or at the termination procedure as follows:

Wound bleeding—None, Minor, Moderate, or Significant.

Gross observations—Dry (dull/not shiny), Moist (glistening in appearance), Wet (presence of fluid), Eschar (tissue appearing dark and leathery), Slough (removable yellowish layer) and its location(s) in the wound site.

Discharge—None, Serous (thin, watery, clear) Serosanguineous (thin, pale red to pink), Sanguineous (thin, bright red), Purulent (opaque tan to yellow, thin or thick).

Dressing and Tissue Retention

Dressing retention (small particles and large pieces) was assessed following dressing removal or peel testing. After removal of the dressings from the wound, dressing retention in the wound was visually assessed and documented. All removed dressings was visually assessed for tissue retention and digitally photographed.

Figure 10:
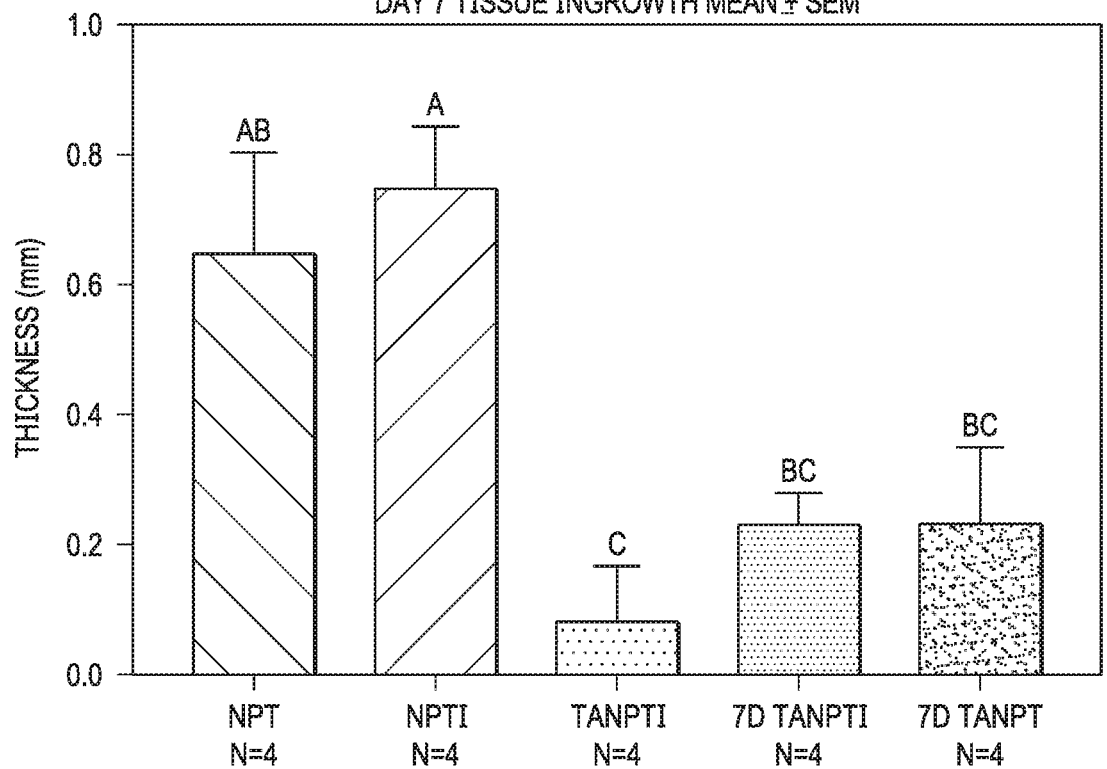
FIG. 10 is a graphical representation of tissue ingrowth measurements. Thickness (mm) is measured for each test and control dressing.

FIG. 10 demonstrates that there was a significant reduction in tissue ingrowth with TANPT and TANPTI.

Histopathology

If wound sites were in 70% ethanol they were immediately processed and if received in NBF wounds were transferred to 70% ethanol for a period of time before further processing per Histopathology Test Site standard procedures. The wound site+dressings (if intact), were embedded in oversized paraffin blocks, entire en bloc site was cross sectioned once at ~5 µm thickness and resulting slides stained with Hematoxylin and Eosin (H&E). Gross images were taken of the cut surface of the specimens prior to processing and embedding in paraffin. In order to accommodate the entire tissue section with border of non-affected skin on all sides, oversized slides were used.

The histopathological response was scored semi-quantitatively by a board-certified veterinary pathologist, on a scale of 1-5 where 1=minimal, 2=mild, 3=moderate, 4=marked and 5=severe, except where otherwise specified. Microscopic evaluation of all stained sections for morphological changes for the wound including, but not limited to, granulation tissue thickness and character, amount of granulation tissue embedded in dressing (if possible), tissue inflammation, edema, vascularity (if possible), presence of bacteria, necrosis and other relevant factors as determined by the pathologist. The peri-wound area was evaluated for characteristics consistent with maceration as determined by the pathologist.

2D Photographs of Individual Wound Sites

Two dimensional (2-D) photographs of the individual wound sites were taken at the following time points:

Day 0 (freshly created wounds)—all wounds

Day 4 (day of dressing change or termination as applicable) after dressing removal and before application of new dressings—all wounds 2-D photographs of the freshly removed dressing next to the wound were taken.

Day 7 after dressing removal and before euthanasia.

2-D photographs of the freshly removed dressing next to the wound were taken.

Histopathological Assessment of Individual Wound Sites

Figure 11:
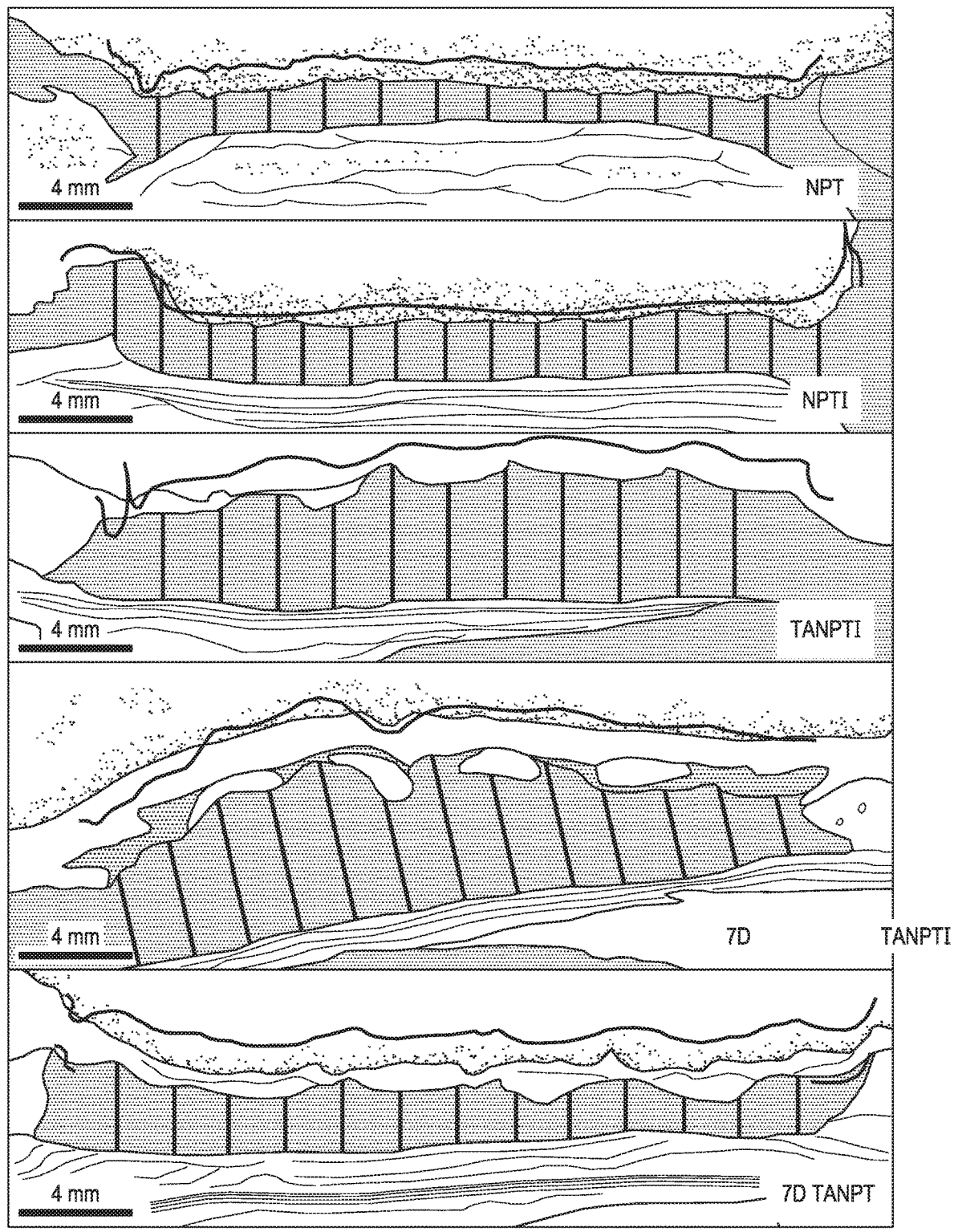
FIG. 11 is an optical micrograph picture demonstrating granulation tissue thickness for each test and control dressing.

The optical micrographs pictures in FIG. 11 demonstrate that TANPT had significantly more granulation than NPT and NPTI.

Figure 12:
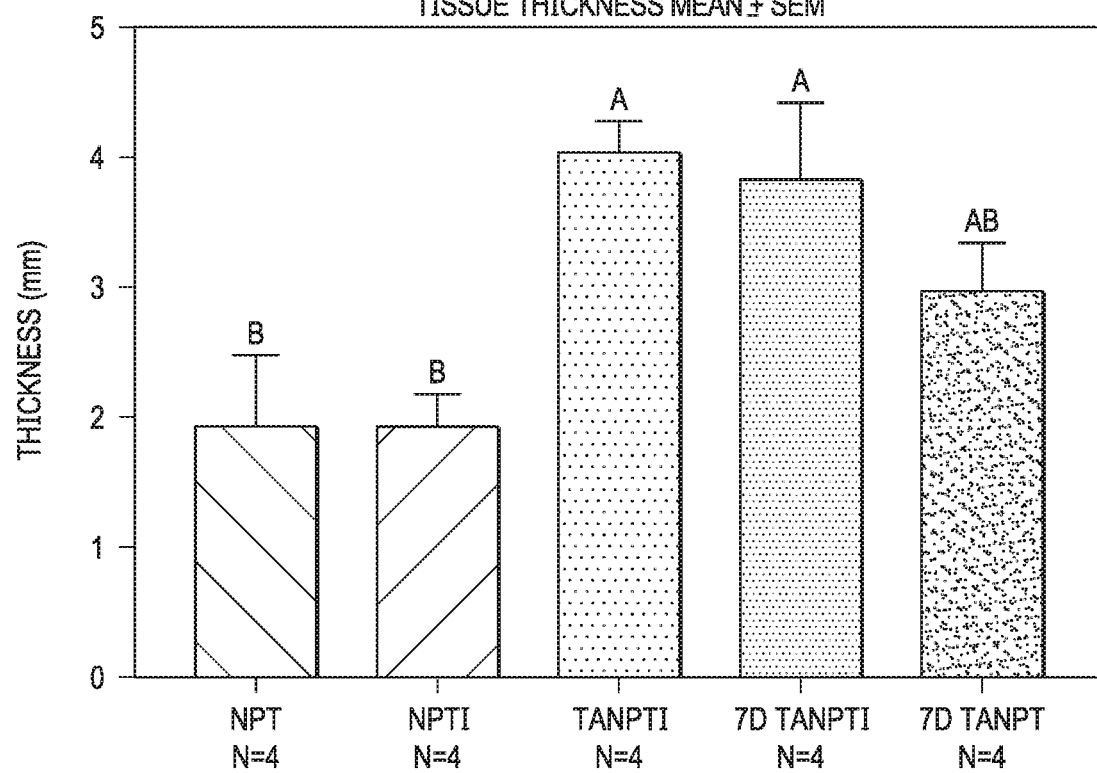
FIG. 12 is a graphical representation of FIG. 11 demonstrating quantitative morphometry granulation tissue thickness for each test and control dressing.

Further FIG. 12 is a graphical representation comparing the Day 7 granulation tissue thickness between the test and control treatments. TANPT and TANPTI showed significantly higher granulation tissue thickness.

Study Conclusions

The data demonstrate that the test article had surprisingly positive results, with improvement when combined with V.A.C. VERAFLO™ Therapy. The test article with V.A.C. VERAFLO™ Therapy performed superiorly by showing an increase in granulation tissue thickness, a reduction in tissue ingrowth, percent epithelialization and average vascularization score.

Additionally, by Day 7, all treatments with the test article showed significantly greater granulation tissue than NPT and NPTI. The percent increase in granulation depth using the test article (measured after a 7 day treatment period) was at least 75% for NPT, and 200% for NPTI. No evidence of adverse events or safety concerns were found. Periwound tissue moisture decreased over time (all treatment groups) reducing risk of maceration.

All treatments with the test article also showed surprising reductions in tissue in-growth, as evidenced by the significant reductions in peel force. After 7 days of either continuous V.A.C.® Therapy or V.A.C. VERAFLO™ Therapy with no dressing change, a peel force of less than 2N was needed to remove the test article. Specifically, a peel force of 1.8N was used to remove the TANPTI test article, and a peel force of 1.5N was used to remove the TANPT test article. Compared to CA1 with V.A.C.® Therapy, the peel force was reduced by 87% and 89%, respectively.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context.

Features, elements, and aspects described in the context of some embodiments may also be omitted, combined, or replaced by alternative features serving the same, equivalent, or similar purpose without departing from the scope of the invention defined by the appended claims. For example, one or more of the features of some layers may be combined with features of other layers to provide an equivalent function. Alternatively or additionally, one or more of the fluid restrictions 220 may have shapes similar to shapes described as exemplary for the valves 605.

Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. Certain features, elements, or aspects may be omitted from the claims if not necessary to distinguish the novel and inventive features from what is already known to a person having ordinary skill in the art.

What is claimed is:

1. A dressing for treating a tissue site with negative pressure, the dressing comprising:
   a first layer comprising a polymer film having a plurality of fluid restrictions through the polymer film that are configured to expand in response to a pressure gradient across the polymer film;
   a second layer coupled to the first layer, the second layer comprising a manifold, wherein the first layer is configured to be interposed between the manifold and the tissue site and at least partially exposed to the tissue site;
   a third layer coupled to the second layer opposite the first layer, the third layer comprising a polymer drape; and
   a fourth layer coupled to the first layer opposite the second layer and comprising a gel including a plurality of apertures, wherein a dimension of one or more of the fluid restrictions through the polymer film exceeds a dimension of at least one of the plurality of apertures.

2. The dressing of claim 1, wherein the fourth layer comprises a hydrophobic gel.

3. The dressing of claim 2, wherein the third layer and the fourth layer enclose the first layer and the second layer.

4. The dressing of claim 2, wherein the third layer and the fourth layer enclose the first layer and the second layer, and the fourth layer is adapted to contact the tissue site.

5. The dressing of claim 2, wherein the hydrophobic gel is a silicone gel.

6. The dressing of claim 1, wherein the plurality of apertures in the fourth layer are in registration with at least some of the plurality of fluid restrictions in the first layer.

7. The dressing of claim 1, wherein the plurality of apertures are in registration with the fluid restrictions.

8. The dressing of claim 1, wherein the plurality of apertures each expose at least a portion of one of the fluid restrictions.

9. The dressing of claim 1, wherein the plurality of apertures in the fourth layer are coextensive with the second layer, and wherein substantially all the plurality of apertures are in registration with the fluid restrictions in the first layer.

10. The dressing of claim 1, wherein the fourth layer is configured to be interposed between the manifold and the tissue site.

11. The dressing of claim 1, wherein one or more of the fluid restrictions comprises a slot including a length that exceeds the dimension of at least one of the plurality of apertures such that the slot overlaps an edge of the at least one of the plurality of apertures.

12. The dressing of claim 1, wherein each of the apertures are sized to expose no more than two of the fluid restrictions.

13. The dressing of claim 1, wherein the fourth layer comprises an area density less than 300 grams per square meter.

14. The dressing of claim 1, wherein the polymer drape comprises a margin that extends beyond the first layer and the second layer, and an adhesive layer disposed in the margin.

15. The dressing of claim 1, wherein the manifold comprises a foam.

16. The dressing of claim 15, wherein the foam is reticulated and has a free volume of at least 90%.

17. The dressing of claim 15, wherein the foam is porous and has an average pore size in a range of 400-600 microns.

18. The dressing of claim 1, wherein the manifold has a thickness less than 7 millimeters.

19. The dressing of claim 1, wherein the manifold is hydrophobic.

20. The dressing of claim 1, wherein the polymer film is hydrophobic.

21. The dressing of claim 20, wherein the polymer film has a contact angle with water greater than 90 degrees.

22. The dressing of claim 20, wherein the polymer film is a polyethylene film.

23. The dressing of claim 1, wherein the fluid restrictions comprise a plurality of slots, each of the slots having a length less than 4 millimeters.

24. The dressing of claim 1, wherein the fluid restrictions comprise a plurality of slots, each of the slots having a width less than 2 millimeters.

25. The dressing of claim 1, wherein the fluid restrictions comprise a plurality of slots, each of the slots having a length less than 4 millimeters and a width less than 2 millimeters.

26. The dressing of claim 1, wherein the fluid restrictions are coextensive with the polymer film.

27. The dressing of claim 1, wherein the fluid restrictions are coextensive with the manifold.

28. The dressing of claim 1, wherein a tissue-facing surface of the dressing is smooth.

* * * * *